United States Patent
Burnam

(10) Patent No.: US 12,097,171 B2
(45) Date of Patent: *Sep. 24, 2024

(54) PETROLATUM-BASED PHMB COMPOSITIONS AND METHODS OF TREATMENT FOR ONYCHOMYCOSIS

(71) Applicant: GLOBAL HEALTH SOLUTIONS LLC, Rome, GA (US)

(72) Inventor: Bradley Burnam, Calabasas, CA (US)

(73) Assignee: GLOBAL HEALTH SOLUTIONS LLC

(*) Notice: Subject to any disclaimer, the term of this patent is extended or adjusted under 35 U.S.C. 154(b) by 0 days.

This patent is subject to a terminal disclaimer.

(21) Appl. No.: 17/467,406

(22) Filed: Sep. 6, 2021

(65) Prior Publication Data

US 2021/0393555 A1 Dec. 23, 2021

Related U.S. Application Data

(63) Continuation of application No. 16/745,280, filed on Jan. 16, 2020, now Pat. No. 11,110,071, which is a continuation-in-part of application No. 15/167,044, filed on May 27, 2016, now Pat. No. 10,675,243.

(60) Provisional application No. 62/793,309, filed on Jan. 16, 2019, provisional application No. 62/338,995, filed on May 19, 2016, provisional application No. 62/326,150, filed on Apr. 22, 2016, provisional application No. 62/319,449, filed on Apr. 7, 2016, provisional application No. 62/182,034, filed on Jun. 19, 2015.

(51) Int. Cl.
| | | |
|---|---|---|
| A61K 31/155 | (2006.01) | |
| A61K 9/00 | (2006.01) | |
| A61K 45/06 | (2006.01) | |
| A61K 47/06 | (2006.01) | |
| A61P 31/10 | (2006.01) | |

(52) U.S. Cl.
CPC .......... *A61K 31/155* (2013.01); *A61K 9/0014* (2013.01); *A61K 47/06* (2013.01); *A61P 31/10* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 2,640,801 A | 6/1953 | Burkhart et al. | |
| 4,895,452 A | 1/1990 | Yiournas et al. | |
| 5,466,463 A | 11/1995 | Ford | |
| 5,994,300 A | 11/1999 | Bayne et al. | |
| 6,248,338 B1 | 6/2001 | Müller et al. | |
| 6,309,664 B1 | 10/2001 | Mathur et al. | |
| 7,074,459 B2 | 7/2006 | Stockel | |
| 7,365,200 B2 | 4/2008 | Sircar et al. | |
| 8,323,674 B2 | 12/2012 | Antoni-Zimmermann et al. | |
| 2002/0146440 A1 | 10/2002 | Smith | |
| 2005/0019431 A1 | 1/2005 | Modak et al. | |
| 2005/0048020 A1 | 3/2005 | Willie | |
| 2006/0051385 A1 | 3/2006 | Scholz | |
| 2007/0020213 A1 | 1/2007 | Tamarkin et al. | |
| 2007/0048345 A1 | 3/2007 | Huang et al. | |
| 2007/0141091 A1 | 6/2007 | Xia et al. | |
| 2008/0279944 A1 | 11/2008 | Sawhney | |
| 2008/0287336 A1 | 11/2008 | Patel et al. | |
| 2009/0136435 A1 | 5/2009 | Mulvanerty | |
| 2009/0269394 A1 | 10/2009 | Baker, Jr. et al. | |
| 2009/0281013 A1 | 11/2009 | Patel et al. | |
| 2010/0092526 A1 | 4/2010 | Baker, Jr. et al. | |
| 2010/0203139 A1 | 8/2010 | Baker, Jr. et al. | |
| 2010/0233224 A1 | 9/2010 | Ramadurai et al. | |
| 2011/0002820 A1 | 1/2011 | Dawson et al. | |
| 2011/0052656 A1 | 3/2011 | Whitekettle et al. | |
| 2011/0251285 A1 | 10/2011 | Tien et al. | |
| 2013/0011342 A1 | 1/2013 | Tamarkin et al. | |
| 2013/0150765 A1 | 6/2013 | Moghe et al. | |
| 2014/0248219 A1 | 9/2014 | Tamarkin et al. | |
| 2014/0276493 A1 | 9/2014 | Leung et al. | |
| 2016/0206567 A1* | 7/2016 | Ridden | A61K 9/0014 |
| 2017/0232004 A1 | 8/2017 | Genberg et al. | |
| 2018/0008711 A1 | 1/2018 | Selner | |
| 2018/0036236 A1 | 2/2018 | Selner | |

FOREIGN PATENT DOCUMENTS

| | | |
|---|---|---|
| CN | 1771937 A | 5/2006 |
| CN | 103182070 A | 7/2013 |
| EP | 1872788 A1 | 1/2008 |
| WO | 2005053617 A2 | 6/2005 |
| WO | 2006099359 A2 | 9/2006 |
| WO | 2013186766 A1 | 12/2013 |

(Continued)

OTHER PUBLICATIONS

European Search Report; European Application No. 16812129.1; mailed Feb. 22, 2019.

Supplementary European Search Report; European Application No. 16812128.3; mailed Mar. 12, 2019.

Hwang, Chiaw-Chi et al., Percutaneous Absorption of Flufenamic Acid in Rabbits; Effect of Dimethyl Sulfoxide and Various Nonionic Surface-Active Agents; Journal of Pharmaceutical Association, U.S., vol. 72, No. 8, Aug. 1983, pp. 857-860.

(Continued)

*Primary Examiner* — David J Blanchard
*Assistant Examiner* — Sarah J Chickos
(74) *Attorney, Agent, or Firm* — Womble Bond Dickinson (US) LLP

(57) ABSTRACT

Compositions and methods for the treatment of onychomycosis. The compositions include a pharmaceutically effective amount of polyhexamethylene biguanide (PHMB), polyaminopropyl biguanide (PAPB), and/or chlorhexidine (CHG) in a petrolatum carrier.

20 Claims, 8 Drawing Sheets

(56) References Cited

FOREIGN PATENT DOCUMENTS

| | | |
|---|---|---|
| WO | 2014183770 A1 | 11/2014 |
| WO | 2015118069 A1 | 8/2015 |
| WO | 2016126982 A1 | 8/2016 |

OTHER PUBLICATIONS

Fuchs, T. et al., "Benzalkoniumchlorid-relevantes Kontaktallergen order Irritans?", Benzalkonium chloride—a relevant contact allergen or irritant?, Results of a multicenter study of the German Contact Allergy Group l Hautartz, Springer Verlag, Berlin, DE, vol. 44, No. 11, Nov. 1993, pp. 699-702.

* cited by examiner

PETROLATUM-BASED PHMB COMPOSITIONS AND METHODS OF TREATMENT FOR ONYCHOMYCOSIS

CROSS-REFERENCE TO RELATED APPLICATIONS

This application is a continuation of U.S. patent application Ser. No. 16/745,280, now U.S. Pat. No. 11,110,071, filed Jan. 16, 2020, which is a continuation-in-part of U.S. patent application Ser. No. 15/167,044, now U.S. Pat. No. 10,675,243, filed May 27, 2016, which claims priority to U.S. Provisional Application No. 62/182,034, filed Jun. 19, 2015, U.S. Provisional Application No. 62/319,449, filed Apr. 7, 2016, U.S. Provisional Application No. 62/326,150, filed Apr. 22, 2016, and U.S. Provisional Application No. 62/338,995, filed May 19, 2016. This application also claims the benefit of U.S. Provisional Application Ser. No. 62/793,309, entitled "Petrolatum-Based PHMB Compositions and Methods of Treatment for Onychomycosis," filed Jan. 16, 2019. The contents of each of the aforementioned patent applications are incorporated by reference herein, for all purposes, in their entirety.

FIELD

The present disclosure is broadly concerned with petrolatum-based cationic-biocide compositions for the treatment and prevention of onychomycosis. The disclosure is also concerned with methods for the treatment of onychomycosis using petrolatum-based polihexanide biguanide (PHMB) compositions.

BACKGROUND

Onychomycosis, also known as tinea unguium, is a highly prevalent fungal infection of the nail affecting 35 million people in the United States. Without treatment, onychomycosis may damage the nail unit and spread to other fingers or toes and skin. Onychomycosis affects 1 in 3 diabetics and increases the risk of secondary infections which may lead to foot disorders and limb amputations. Since, onychomycosis is generally a non-life threatening infection, it should ideally be treated topically. However, current topical treatments do not penetrate the nail plate rendering them ineffective due to an inability to reach microbes below the nail plate. The use of oral medications for onychomycosis are limited by safety concerns including liver toxicity, drug-drug interactions, loss of taste, and migraine headaches. As a result, 85% of the 1 in 10 Americans affected by onychomycosis fail to seek treatment due to limited safe and effective treatment options. Accordingly, additional compositions and methods for the treatment of onychomycosis are desirable.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION

Figure 1:
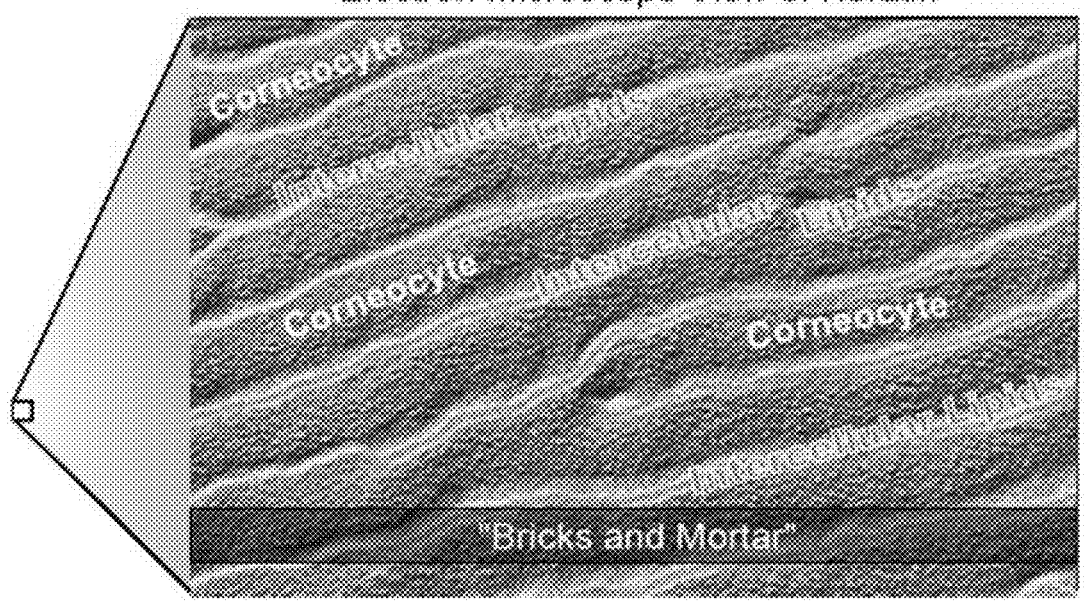
FIG. 1 depicts an electron microscope micrograph showing the structure of typical nails, according to an exemplary embodiment of the present disclosure.
Figure 2:
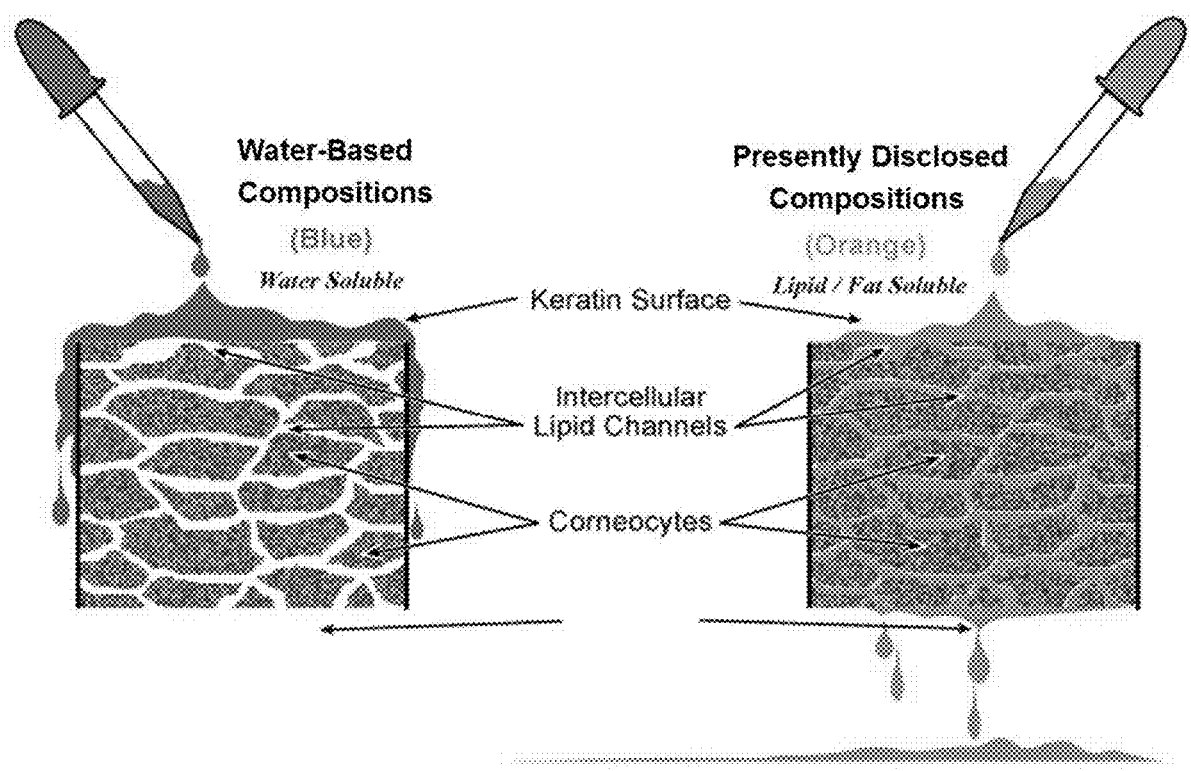
FIG. 2 is a diagrammatic view depicting penetration of the presently disclosed topical compositions through the nail to deliver PHMB and optionally other anti-fungal agents to the site of infection below the nail, according to an exemplary embodiment of the present disclosure.

The present disclosure provides compositions and methods for the treatment of onychomycosis. It has been unexpectedly discovered that the presently disclosed compositions comprising polyhexamethylene biguanide (PHMB) are effective in the treatment of onychomycosis. In particular, it has been unexpectedly discovered that the presently disclosed compositions are capable of penetrating the keratin surface and nail plate to deliver a pharmaceutically effective amount of PHMB directly to the site of infection. In particular, as depicted in FIG. 1, the presently disclosed compositions are capable of penetrating the keratin surface of the nail to carry active ingredients, such as PHMB, through the channels of the lipid bilayers and deliver the active ingredients to the nail bed and throughout the nail itself. FIG. 1 depicts an electron micrograph of skin or nail comprising corneocytes interspaced by intercellular lipid bilayers. As shown in FIG. 2, water-based topical formulations cannot penetrate the corneocytes nor pass through the intercellular lipids interspersed between the corneocytes. However, the presently disclosed petrolatum-based compositions are capable of passing through the intercellular lipid channels to penetrate the epidermal layer and enable deep delivery of antifungal ingredients, such as PHMB, to the site of the infection below the nail.

According to at least one aspect of the present disclosure, a method of treating onychomycosis in a subject is provided. The method may include applying a petrolatum-based polyhexamethylene biguanide (PHMB) composition to the nail of a subject in need of treatment. The petrolatum-based PHMB composition may include, for example, a pharmaceutically effective amount of polyhexamethylene biguanide (PHMB) in a petrolatum carrier.

In at least some instances, the onychomycosis may be distal subungual onychomycosis, or white superficial onychomycosis (WSO), or proximal subungual onychomycosis, or Candidal onychomycosis. In some cases, the onychomycosis may be caused by *Trichophyton rubrum* (*T. rubrum*), or caused by *Candida*, or caused by *Candida auris* (*C. auris*). In at least some instances, the onychomycosis may be caused by multi-drug resistant *C. auris*.

The petrolatum-based PHMB composition may include, for example, greater than about 80% by weight petrolatum, or greater than about 90% by weight petrolatum, or greater than about 95% by weight petrolatum. The petrolatum-based PHMB composition may also include from about 0.005% to about 5% by weight PHMB, or from about 0.01% to about 5% by weight PHMB, or from about 0.05% to about 5% by weight PHMB, or from about 0.05% to about 3% by weight PHMB, or from about 0.1% to about 1% by weight PHMB, or from about 0.2% to about 0.6% by weight PHMB, or from about 0.3% to about 0.5% by weight PHMB, or from about 0.1% to about 3.5% by weight PHMB, or from about 0.05% to about 2.5% by weight PHMB, or from about 0.5% to about 3% by weight PHMB, or from about 0.5% to about 2.5% by weight PHMB, or from about 1.5% to about 2.5% by weight PHMB. In at least some instances, the petrolatum-based PHMB composition contains no emulsifier. In other instances, the petrolatum-based PHMB composition excludes an added emulsifier. As used herein, the term "added emulsifier" refers to an emulsifier in addition to the presently claimed components of the petrolatum-based PHMB composition.

PHMB is closely related to the polymeric biguanide polyaminopropyl biguanide (PAPB). Therefore, in at least some instances, a pharmaceutically effective amount of polyaminopropyl biguanide (PAPB) may be substituted for the pharmaceutically effective amount of PHMB in the presently disclosed compositions and methods. For example, the petrolatum-based PHMB composition may include from about 0.005% to about 5% by weight PAPB, or from about 0.01% to about 5% by weight PAPB, or from about 0.05% to about 5% by weight PAPB, or from about 0.05% to about 3% by weight PAPB, or from about 0.1% to about 1% by weight PAPB, or from about 0.2% to about 0.6% by weight PAPB, or from about 0.3% to about 0.5% by weight PAPB, or from about 0.1% to about 3.5% by weight PAPB, or from about 0.05% to about 2.5% by weight PAPB, or from about 0.5% to about 3% by weight PAPB, or from about 0.5% to about 2.5% by weight PAPB, or from about 1.5% to about 2.5% by weight PAPB.

According to one aspect of the present disclosure, PHMB may be the only antifungal agent included in the petrolatum-based PHMB composition, in at least some instances. As used herein, the term "antifungal agent" refers to any chemical agent that exhibits antifungal activity. In such instances where PHMB is the only antifungal agent included in the petrolatum-based PHMB composition, the petrolatum-based PHMB composition may also include from about from about 0.05% to about 5% by weight PHMB, or from about 0.05% to about 3% by weight PHMB, or from about 0.1% to about 1% by weight PHMB, or from about 0.2% to about 0.6% by weight PHMB, or from about 0.3% to about 0.5% by weight PHMB, or from about 0.1% to about 3.5% by weight PHMB, or from about 0.05% to about 2.5% by weight PHMB, or from about 0.5% to about 3% by weight PHMB, or from about 0.5% to about 2.5% by weight PHMB, or from about 1.5% to about 2.5% by weight PHMB.

In at least some instances, chlorhexidine may be substituted for some portion of the PHMB or PAPB present in the petrolatum-based PHMB composition. In at least some instances, the petrolatum-based PHMB composition may further include a cationic biocide selected from the group consisting of benzalkonium chloride, cetrimide, chlorhexidine, and any combination thereof. In at least some instances, the petrolatum-based PHMB composition may further include a preservative selected from the group consisting of benzalkonium chloride, cetrimide, chlorhexidine, and any combination thereof. In some instances, the petrolatum-based PHMB composition may include from about 0.001% to about 0.01% by weight benzalkonium chloride (BZK), or from about 0.001% to about 0.15% by weight BZK, or from about 0.005% to about 0.007% by weight BZK. In at least some instances, the BZK is included as a preservative in the petrolatum-based PHMB composition. In at least some instances, the petrolatum-based PHMB composition may be prepared by a process that includes: (a) dissolving the PHMB in a polar solvent to give a PHMB solution; (b) heating the petrolatum to a temperature sufficient to cause the petrolatum to melt to give a melted petrolatum and heating the PHMB solution to a temperature higher than the temperature of the melted petrolatum to give a heated PHMB solution; (c) mixing the melted petrolatum and the heated PHMB solution to give a melted mixture; and (d) cooling the melted mixture to give the petrolatum-based PHMB composition. In some instances, the heated PHMB solution may have a temperature that is about 1° C. to about 5° C. higher than the temperature of the melted petrolatum. In some instances, the PHMB is dissolved in a polar solvent to form a PHMB solution and the PHMB solution is dispersed in the petrolatum to form a stable suspension. The polar solvent may be, for example, water, ethanol, or any combination of water and ethanol.

According to at least one aspect of the present disclosure, the petrolatum-based PHMB compositions may further include one or more additional anti-fungal agents selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof. In some instances, the petrolatum-based PHMB composition may include just one additional anti-fungal agent. In such instances, the petrolatum-based PHMB composition may include from about 0.5% to about 5% by weight, or from about 0.5% to about 1.5% by weight, or from about 0.75% to about 1.25% by weight, or from about 0.5% to about 2.5% by weight additional anti-fungal agent based on the total weight of the petrolatum-based PHMB composition. In other instances, the petrolatum-based PHMB composition may include more than one additional anti-fungal agents. In such instances, the total weight of the additional anti-fungal agents in the petrolatum-based PHMB composition may be from about 0.5% to about 5% by weight, or from about 0.5% to about 1.5% by weight, or from about 0.75% to about 1.25% by weight, or from about 0.5% to about 2.5% by weight based on the total weight of the petrolatum-based PHMB composition.

In at least some instances, the petrolatum-based PHMB compositions may include from about 0.01% to about 5% by weight terbinafine HCl, or from about 0.01% to about 5% by weight ciclopirox, or from about 0.01% to about 5% by weight ciclopirox olamine, or from about 0.01% to about 5% by weight fluconazole, or from about 0.01% to about 5% by weight itraconazole, or from about 0.01% to about 5% by weight ketoconazole, or from about 0.01% to about 5% by weight amorolfine, or from about 0.01% to about 5% by weight efinaconazole, or from about 0.01% to about 5% by weight clotrimazole, or from about 0.01% to about 5% by weight miconazole (miconazole nitrate), or any combination thereof.

In at least some other instances, the petrolatum-based PHMB compositions may include from about 0.001% to about 5% by weight terbinafine HCl, or from about 0.001% to about 5% by weight ciclopirox, or from about 0.001% to about 5% by weight ciclopirox olamine, or from about 0.001% to about 5% by weight fluconazole, or from about 0.001% to about 5% by weight itraconazole, or from about 0.001% to about 5% by weight ketoconazole, or from about 0.001% to about 5% by weight amorolfine, or from about 0.001% to about 5% by weight efinaconazole, or from about 0.001% to about 5% by weight clotrimazole, or from about 0.001% to about 5% by weight miconazole (miconazole nitrate), or any combination thereof.

In cases in which one or more additional anti-fungal agents are included in the composition, the one or more additional anti-fungal agents may be dissolved along with the PHMB in a polar solution or solvent to form a PHMB solution and added and mixed with the melted petrolatum as described above. In such cases, the PHMB solution may include PHMB and at least one additional anti-fungal agent selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof, dissolved in the polar solvent.

In other instances, the one or more additional anti-fungal agents may be added to the petrolatum-based PHMB composition in powdered form after the PHMB solution is mixed with the melted petrolatum. In at least some instances, petrolatum-based PHMB composition may be melted and the one or more additional anti-fungal agents added in powdered form to the melted petrolatum-based PHMB composition.

According to at least one aspect of the present disclosure, the petrolatum-based PHMB composition may be a petrolatum-based composition that includes petrolatum and a pharmaceutically effective amount of PHMB. In such cases, the compositions may include, for example, greater than about 80% by weight petrolatum. The compositions may also include a polar solvent. The polar solvent may comprise from about 1% to about 15% by weight, or from about 1% to about 5% by weight, or from about 1% to about 10% by weight, or from about 1% to about 7% by weight, or from about 2.5% to about 5% by weight, or from about 2% to about 6% by weight of the petrolatum-based PHMB composition. In some instances, the polar solvent may be water. In other instances, the polar solvent may be ethanol. It has unexpectedly been found that ethanol can serve as a nail penetration enhancer when used a portion of the polar solvent in the petrolatum-based PHMB compositions. In still other instances, the polar solvent may be a mixture of water and ethanol, in any proportion, but preferably in a water to ethanol ratio of from about 60:40 to about 90:10 by weight. In at least some instances, ethanol may comprise from about 10% to about 40% by weight of the PHMB solution. When used as polar solvent, ethanol may comprise from about 0.01% to about 6.5% by weight, or from about 0.5% to about 2.5% by weight, or from about 0.5% to about 1.5% by weight of the petrolatum-based PHMB composition.

In certain cases, the PHMB, and optionally an additional anti-fungal agent, and the polar solvent may be dispersed in the petrolatum in the form of nanodroplets. According to at least one aspect, the petrolatum-based PHMB compositions contain no emulsifier. In some instances, the PHMB, and optionally an additional anti-fungal agent, may be dissolved in a polar solvent to form a PHMB solution and the PHMB solution dispersed in the petrolatum. In such cases, the PHMB solution may be dispersed in the petrolatum to form a stable suspension such that the PHMB solution does not separate from the petrolatum for at least six months. According to at least one aspect of the present disclosure, the resultant petrolatum-based PHMB composition does not require an emulsifier to form a stable suspension of PHMB dispersed in the petrolatum. Further, the petrolatum-based PHMB composition prepared according to this process does not require high shear mixing to form a stable suspension of PHMB in petrolatum in the absence of an added emulsifier.

I. Compositions

According to one aspect, the present disclosure provides for compositions that are petrolatum-based. A petrolatum-based composition is made up primarily of petrolatum. The characteristics of a petrolatum-based composition differ from a composition containing only a small amount of petrolatum. In some embodiments, the petrolatum-based composition is greater than about 80% petrolatum. In other embodiments, the petrolatum-based composition is greater than about 81% petrolatum, greater than about 82% petrolatum, greater than about 83% petrolatum, greater than about 84% petrolatum, greater than about 85% petrolatum, greater than about 86% petrolatum, greater than about 87% petrolatum, greater than about 88% petrolatum, greater than about 89% petrolatum, greater than about 90% petrolatum, greater than about 91% petrolatum, greater than about 92% petrolatum, greater than about 93% petrolatum, greater than about 94% petrolatum, greater than about 95% petrolatum, greater than about 96% petrolatum, greater than about 97% petrolatum, greater than about 98% petrolatum, or greater than about 99% petrolatum. The petrolatum is preferably medical grade petrolatum.

The composition also contains PHMB dispersed throughout the petrolatum. PHMB is the composition ingredient active in treating onychomycosis. In addition to PHMB, the compositions may also include other cationic biocides, such as quaternary ammonium compounds, bisbiguanides, and polymeric biguanides. In particular, other cationic biocides that may be included in the compositions may include, but are not limited to, benzalkonium chloride, cetrimide, chlorhexidine, polihexanide biguanide (polihexanide, polyhexamethylene guanide, poly(iminoimidocarbonyl-iminoimidocarbonyl-iminohexamethylene), poly(hexamethylenebiguanide), polyaminopropyl biguanide) and salts or combinations thereof. In one embodiment, the composition contains a mixture of polihexanide biguanide (PMHB) and benzalkonium chloride (BZK) preservative. The total amount of cationic biocide in the composition generally constitutes less than about 1% by weight of the total composition. In preferred embodiments, the cationic biocide constitutes from about 0.1% to about 0.5% by weight, or more preferably, from about 0.1% to about 0.3% by weight to the total composition.

The remaining weight of the composition, typically from about 0.1% to about 6% by weight of the petrolatum-based composition, is liquid. In one embodiment, the composition contains about 5% water.

The PHMB and other cationic biocides that may be used do not react with the petrolatum. Instead, the PHMB and other cationic biocides and/or other antifungal agents that may be included in the compositions are dispersed in the petrolatum as nanodroplets, and the petrolatum serves as a suspension matrix for the PHMB and other cationic biocides. "Nanodroplet," as used herein, is an aggregation of PHMB and optionally any cationic biocide molecules or antifungal agents in the petrolatum base. The nanodroplets typically contain a small amount of water in addition to the PHMB and other optional cationic biocides or additional antifungal agents. Nanodroplets in accordance with the present disclosure are shown in FIG. 1. The nanodroplets may vary in size but generally the longest dimension of the nanodroplets measures from about 10 nm to about 10,000 nm. In various embodiments, the nanodroplets range from about 10 nm to about 100 nm, from about 100 nm to about 1000 nm, from about 1000 nm to about 2000 nm, from about 2000 nm to about 3000 nm, from about 3000 nm to about 4000 nm, from about 4000 nm to about 5000 nm, from about 5000 nm to about 6000 nm, from about 6000 nm to about 7000 nm, from about 7000 nm to about 8000 nm, from about 8000 nm to about 9000 nm, from about 9000 nm to about 10,000 nm. The nanodroplets are dispersed through the petrolatum homogeneously.

Surprisingly, embodiments of the present invention do not require an emulsifier. An emulsifier, as used herein, is an added formulation ingredient used to reduce the tension between hydrophilic and hydrophobic surface ingredients, thereby facilitating the mixture hydrophilic and hydrophobic ingredients. Prior to the present invention, those skilled in the art expected that an emulsifier would be needed to disperse cationic biocides, such as PHMB, which are polar, as well as additional anti-fungal agents, in a non-polar petrolatum suspension matrix. Where an emulsifier is used, the emulsifier may have a hydrophilic-lipophilic balance (HLB) of less than 10.

The compositions described herein are stable. In one aspect, stability refers to the integrity of the composition as a whole, and in particular, the stability of the nanodroplets in the petrolatum. Under ambient conditions, the petrolatum and the cationic biocides will not separate for greater than two years, meaning that the composition is shelf stable for at least two years. Even under accelerated conditions, such as reduced pressure, the petrolatum and the PHMB and any other cationic biocides do not separate, but rather the PHMB and cationic biocides, and optional additional anti-fungal agents, remain suspended as nanodroplets in the petrolatum. In addition to the stability of the nanodroplets within the composition, the compositions described herein also show exceptional chemical stability for the PHMB and other cationic biocides. The chemical stability stems primarily from the low-temperature manufacturing process described below. The absence of excessive heat conditions in the manufacturing of the compositions improves the chemical stability (resistance to degradation) for the PHMB and other cationic biocides.

In some embodiments, the petrolatum-based compositions described herein consist essentially of petrolatum, PHMB, and water. In one preferred embodiment, the petrolatum-based compositions consist essentially of petrolatum, benzalkonium chloride, polihexanide biguanide, and water. In alternative embodiments, the petrolatum-based compositions described herein consist of petrolatum, a cationic biocide, and water or consist of petrolatum, benzalkonium chloride, polihexanide biguanide, and water.

In other embodiments, the petrolatum-based compositions described herein may further comprise a compound that stimulates healing. More specifically, the petrolatum-based compositions described herein may further comprise a compound that stimulates healing for use in intraoperative applications and chronic wound care applications. Non-limiting examples of compounds that stimulate healing include polycaprolactone-tricalcium phosphate (PCL-TCP), collagen, chitosan, cellulose, thrombin, chondroitin sulfate (CS), chondroitin sulfate succinimidyl succinate (CS-NETS), and growth factors such as TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, or autologous intraoperative biologics such as platelet-rich plasma (PRP) and bone marrow (BM).

In other embodiments, the petrolatum-based compositions described herein may further comprise a dermatologically acceptable carrier. A "dermatologically-acceptable carrier," as used herein, is a component or components suitable for use in contact with human keratinous tissue without undue toxicity, incompatibility, instability, allergic response, and the like. Where employed, the carrier is inert in the sense of not bringing about a deactivation of the active ingredients, and in the sense of not bringing about any adverse effect on the skin areas to which it is applied. Common dermatological additives are also envisioned for some embodiments. In certain embodiments, a dermatological additive is a whitening agent and/or hemostatic agent.

Additionally, the compositions may be incorporated in predetermined therapeutically effective amounts into disposables such as wipes, gauze, patches, wraps, bandages, adhesive strips, sponge, cotton swab, glove, sock, wrist bands, fabric, fibers, sutures, medication pad, underwear, tissue, pain-relief gel pack or bed liner and the like. For instance, the composition may be applied to the surface of, or impregnated into disposables.

II. Process for Making

The disclosure also provides a method for making the compositions described in Section (I). The process comprises: (a) dissolving PHMB in a solvent to give a PHMB solution; (b) heating the petrolatum to a temperature sufficient to give a melted petrolatum, and heating the PHMB solution to a temperature higher than the temperature of the petrolatum to give a heated PHMB solution; (c) mixing the melted petrolatum and the heated PHMB solution to give a melted mixture; and, (d) cooling the melted mixture to give the petrolatum-based composition. As would be appreciated by one of skill in the art, steps (a)-(d) are conducted sequentially.

The PHMB as well any other cationic biocide, selected from the group described in Section (I), is first dissolved in a solvent to give a PHMB/cationic biocide solution. Acceptable solvents for the PHMB/cationic biocide solution include water or other solvents. Generally polar solvents such as water, ethanol, or any combination thereof are used. The PHMB and any other cationic biocides are typically dissolved in the solvent a concentration ranging from about 0.005% to about 5%. Typically, the amount of solvent used is from about 1:10 to about 1:30 the amount of petrolatum and more preferably is about 1:20 to the amount of petrolatum by volume. The amount of PHMB and other cationic biocides can be calculated by one skilled in the art to provide the desired weight percentage for the final composition.

Both the PHMB solution and the petrolatum are heated. The heating of these two ingredients can be conducted at the same time or sequentially so long as the melted petrolatum and the heated PHMB solution are at the appropriate temperatures during the mixing step. Petrolatum is a solid that melts at approximately 37° C. As such, petrolatum may be heated to any temperature at or above 37° C. For instance, the petrolatum may be heated to a temperature ranging from about 37° C. to about 45° C., from about 40° C. to about 50° C., from about 45° C. to about 55° C., from about 50° C. to about 60° C., from about 55° C. to about 65° C., from about 60° C. to about 70° C., from about 65° C. to about 75° C., from about 70° C. to about 80° C., from about 75° C. to about 85° C., from about 80° C. to about 90° C., from about 85° C. to about 95° C., or from about 90° C. to about 100° C. or more. Higher temperatures may also be envisioned. Preferably, the petrolatum is heated to a temperature ranging from about 37° C. to about 55° C., more preferably to a temperature ranging from about 40° C. to about 50° C. Heat may be provided to the petrolatum by any method known in the art, but a water bath or low temperature hot plate are preferred.

The PHMB solution is heated to a temperature above the temperature of the melted petrolatum. Any temperature above the temperature of the melted petrolatum may be used in a method of the present disclosure, provided that the heat does not cause excessive degradation of an active ingredient such as PHMB, or excessive evaporation of the active ingredient or polar solvent. For instance, the PHMB solution may be heated to a temperature that is about 1° C. to about 10° C., about 5° C. to about 15° C., about 10° C. to about 20° C., about 15° C. to about 25° C., about 20° C. to about 30° C., about 25° C. to about 35° C., about 30° C. to about 40° C., about 35° C. to about 45° C., about 40° C. to about 50° C., about 45° C. to about 55° C., about 50° C. to about 60° C. or about 65° C. or about 75° C. higher than the temperature of the melted petrolatum. Higher temperatures may also be envisioned. Preferably, the PHMB solution is heated to a temperature that is about 1° C. to about 10° C. higher than the temperature of the melted petrolatum. In another embodiment, the PHMB solution is heated to a temperature that is about 1° C. to about 5° C. higher than the melted petrolatum. In still other embodiments, the PHMB solution is heated to a temperature that is about 1° C., 2° C., 3° C., 4° C., or 5° C. above the temperature of the melted petrolatum. Again, the heating can be provided by any means known in the art but is preferably provided by a water bath or low temperature hot plate.

Once both the petrolatum and the PHMB solution are heated as described above, the melted petrolatum and the heated PHMB solution are mixed to give a melted mixture containing petrolatum and the heated PHMB solution. The mixing can be accomplished by a variety of methods including homogenization, acoustic mixing, and high RPM mixing. Depending on the batch size, the size of the mixer, and the type of mixing, the mixing may be conducted for several minutes or more. When mixed in accordance with the parameters disclosed above, the melted petrolatum and the heated PHMB solution fuse in the melted mixture.

After the melted petrolatum and the heated PHMB solution have fused they are allowed to cool and solidify into the composition described more fully in Section (I) ("the final composition"). Cooling may be achieved by reducing the amount of heat provided to the melted mixture, or cooling may be achieved passively under conditions where no heating is added. In some embodiments, cooling is controlled so that the temperature of the melting mixture is gradually lowered to ambient temperatures. The product is preferably packaged a few degrees above its solidification point so that the packaging can be filled by pouring the melted mixture. The composition preferably solidifies to the final composition in the package. The package is sealed after this solidification.

The process may be conducted with two or more cationic biocides. The cationic biocides may be dissolved in solvent separately or may be dissolved in the same solvent. Addition of additional cationic biocides does not change the process steps above.

III. Methods of Use

In another aspect, the invention encompasses a method of preventing or treating onychomycosis in a subject using the compositions described herein.

The compositions may be applied topically to the nail of a subject in need.

Subjects in need may be those having onychomycosis, including subjects having distal subungual onychomycosis, white superficial onychomycosis (WSO), proximal subungual onychomycosis, and Candidal onychomycosis. The onychomycosis may be caused by, for example, *Trichophyton rubrum* (*T. rubrum*) or *Candida auris* (*C. auris*), including multi-drug resistant *C. auris*. The subject is preferably human but the composition may also be useful in animals, particularly mammals, for example domestic animals, livestock, or other types of animals.

Typically, the composition is applied to the nail of the subject. Application to the nail includes application to a site having onychomycosis as well as to sites that may be susceptible to acquiring onychomycosis. Therefore, the presently disclosed compositions may be applied to skin or nails in order to prevent infection by the causative agent responsible for onychomycosis. The presently disclosed compositions may also be used as a topical dressing to a nail and/or skin of a subject in order to prevent or reduce the occurrence of onychomycosis. As used herein, the terms "applied to the nail" or "applying to the nail," in all their forms, as used throughout this disclosure in reference to applying the presently disclosed compositions to the nail of a subject, refers to all modes of administration of the compositions to the nail and/or nearby skin of a patient including topical administration of the compositions directly to the nail or surrounding skin of a subject or causing contact between the compositions and the nail of a subject through, for instance, a wrap, gauze, or bandage impregnated or containing the presently disclosed compositions.

The amount of composition applied in the methods described herein can and will vary depending on the condition being treated and the severity of that condition.

Generally, the amount used is sufficient to cover the affected nail area with a thin layer of the composition. The composition is applied directly to the nail. In some embodiments, the composition is spread so that it forms a thin layer over the treatment area. In other embodiments, the composition is spread by a melting action that occurs as the warmth of the patient's nail and surrounding skin melts the petrolatum or pharmaceutically acceptable carrier. The composition may be covered with a bandage after application. The compositions may also be impregnated into a bandage or other material that is applied to the treatment area.

The composition when applied to the nail and surrounding skin is non-irritating and non-cytotoxic. These properties allow the composition to be used on sensitive treatment areas. These characteristics also allow for use to treat or prevent onychomycosis over a long period, such as for example 2 weeks, 4 weeks, 6 weeks, 8 weeks, or longer without irritation to the treated area. It will be recognized however, that the compositions may be used for shorter periods of time if necessary.

The compositions are also capable of extended release of the PHMB and optionally other anti-fungal agents to the area of application. "Extended release" as used herein means that the compositions release PHMB and optionally other anti-fungal agents to the application site over a period of time extending past twelve hours. The time over which the extended release is provided is variable depending on the amount of the composition that is applied, but in general, the release of PHMB and optionally other anti-fungal agents is extended beyond the initial application and PHMB and other optional anti-fungal agents has been shown to be released for up to 1 week. This extended release allows the composition to be applied less frequently and improves patient compliance with the treatment.

The compositions of the present disclosure also offer kinetic release when applied to the skin or nails. Kinetic release means that PHMB and other optional anti-fungal agents are released to the treatment area more rapidly when the treatment area is hotter.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Exemplary Formulation Process

Figure 3:
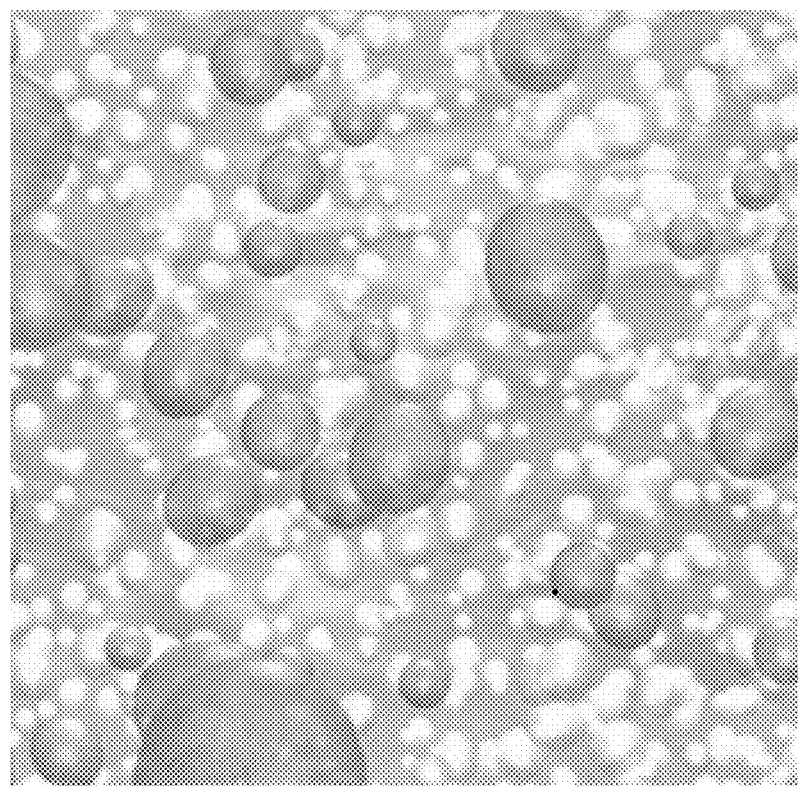
FIG. 3 depicts an image of the formulation structure when using the mixing methodology disclosed herein for permanently encapsulating polyhexamethylene biguanide (PHMB) as nanodroplets into petrolatum without an emulsifier, according to an exemplary embodiment of the present disclosure.

"Formulation 1" (FIG. 3) was prepared by adding 2540.3 pounds of white petrolatum to a tank that has been cleaned and sterilized in accordance with SOP protocol. In the tank was used to heat the petrolatum to 110° C. to 113° F. to melt the petrolatum. In a separate clean and sanitized container 133.70 pounds of water and the desired amount of BZK and PHMB were added and heated to 122° F. When both phases were at temperature, the solution phase was slowly added to the petrolatum with mixing. The heat was decreased slowly to 96 to 104° F. The product was tested for quality control and transferred to polypropylene drums. The resulting composition was shiny and white to slightly yellow in appearance. Specific gravity at 25° C. matches specification when it is from 0.830-0.910. Viscosity at @ 25° C. TF @ 10 rpm matches specification when it is from about 225,000-300,000 cps. The final formulation contained the following ingredients by weight percent: 95% petrolatum, 0.13% BZK, 0.2% PHMB, and 4.67% water.

Example 2. Skin Sensitization Evaluation

A study was conducted on the formulation of Example 1, referred to herein as "Formulation 1" to assess skin sensitization. Patches comprising Formulation 1 were affixed directly to the skin of 53 human study participants representing an age range from 18-63 and five skin types. Table 1 presents the participant demographics. Patches remained in place for 48 hours after the first application. Participants were instructed not to remove the patches prior to their 48 hour scheduled visit. Thereafter, the subjects were instructed to remove patches for 24 hours. This procedure was repeated until a series of nine consecutive, 24 hour exposures had been made three times per week for three consecutive weeks. Test sites were evaluated by trained personnel. Following a 10-14 day rest period, a retest/challenge dose was applied once to a previously unexposed test site. Test sites were evaluated by trained personnel 48 and 96 hours after application. The sites were scored based on the International Contact Dermatitis Research Group scoring scale (Rietschel, Fowler, Ed., Fisher's Contact Dermatitis (fourth ed.). Baltimore, Williams & Wilkins, 1995) as presented in Table 2.

TABLE 1

| Participant Demographics. | |
|---|---|
| Number of subjects enrolled | 53 |
| Number of subjects completing study | 53 |
| Age Range | 18-63 |
| Sex | Male 13 |
| | Female 40 |
| Fitzpatrick Skin Type* | |
| 1 - always burn, does not tan | 0 |
| 2 - burn easily, tan slightly | 4 |
| 3 - burn moderately, tan progressively | 47 |
| 4 - burn a little, always tan | 2 |
| 5 - rarely burn, tan intensely | 0 |
| 6 - never burn, tan very intensely | 0 |

*Agaghe P, Hubert P. Measuring the skin. (p. 473, table 48.1) Springer-Verlag Berlin Heidelberg, 2004.

TABLE 2

| Scoring Scale. | |
|---|---|
| 0 | No reaction (negative) |
| 1 | Erythema throughout at least ¾ of patch area |
| 2 | Erythema and induration throughout at least ¾ of patch area |
| 3 | Erythema, induration and vesicles |
| 4 | Erythema, induration and bullae |
| D | Site discontinued |
| Dc | Subject discontinued |

No adverse reactions of any kind were reported during the course of study. Accordingly, Formulation 1 gives no identifiable signs or symptoms of primary irritation or sensitization (contact allergy).

Example 3. Antimicrobial Efficiency Testing

Antimicrobial efficacy testing was conducted according to USP 51. Five microbes were tested. Each organism was inoculated at an inoculum level of $1\times10^6$ colony forming units (CFU) per gram for bacteria or $1\times10^5$ CFU per gram for yeast and mold. The inoculated samples were then stored at 20-25° C. for 28 days. The population of each microorganism was determined by plate counting at Day 2, 7, 14, 21, and 28. The plate counts were performed at a 1:10 initial dilution using Modified Letheen Broth as the diluent and plated onto Tryptic Soy and Sabouraud Dextrose agar.

A single application of Formulation 1 gave 100% elimination from day 2 to day 28 for all microbes tested (Table 3). Given the 100% elimination, there was a 4 log reduction in the yeast/mold species and a 5 log reduction in the bacterial species (Table 4). Table 5 is a positive control indicating that the method used recovers 80-100% of the microbe in the absence of Formulation 1. Accordingly, the microbes present in the test sample were eliminated under the tested conditions. The results illustrate the broad spectrum of activity for Formulation 1.

TABLE 3

Preservative Testing.

| | | Colony Forming Units/gram | | | | |
|---|---|---|---|---|---|---|
| Organism | Inoculum/g | Day 2 | Day 7 | Day 14 | Day 21 | Day 28 |
| *Staphylococcus aureus* (bacteria) ATCC#6538 | $1 \times 10^6$ | <10 | <10 | <10 | <10 | <10 |
| *Pseudomonas aeruginosa* (bacteria) (ATCC#9027) | $1 \times 10^6$ | <10 | <10 | <10 | <10 | <10 |
| *Escherichia coli* (bacteria) (ATCC#8739) | $1 \times 10^6$ | <10 | <10 | <10 | <10 | <10 |
| *Candida albicans* (yeast) (ATCC#10231) | $1 \times 10^5$ | <10 | <10 | <10 | <10 | <10 |
| *Aspergillus niger* (mold) (ATCC#16404) | $1 \times 10^5$ | <10 | <10 | <10 | <10 | <10 |

TABLE 4

Log Reduction Calculation from Initial Inoculum.

| | 14 days | 28 days |
|---|---|---|
| *Aspergillus niger* | 4.00 | 4.00 |
| *Candida albicans* | 4.00 | 4.00 |
| *Pseudomonas aeruginosa* | 5.00 | 5.00 |
| *Escherichia coli* | 5.00 | 5.00 |
| *Staphylococcus aureus* | 5.00 | 5.00 |

TABLE 5

Preservative Testing Validation.

| Organism | Inoculum | Dilution | Microbial Recovery | Diluent | Percent Recovery |
|---|---|---|---|---|---|
| *Staphylococcus aureus* | 76 cfu/plate | 1:10 | 69 cfu/plate | LB | 87% |
| *Pseudomonas aeruginosa* | 83 cfu/plate | 1:10 | 81 cfu/plate | LB | 97% |
| *Escherichia coli* | 68 cfu/plate | 1:10 | 58 cfu/plate | LB | 85% |
| *Candida albicans* | 63 cfu/plate | 1:10 | 50 cfu/plate | LB | 79% |
| *Aspergillus niger* | 60 cfu/plate | 1:10 | 60 cfu/plate | LB | 100% |

CFU = colony forming units;
LB = Letheen Broth;
Diluent = Letheen Broth;
Dilution: 1:10

Example 3 indicates that the presently disclosed compositions are effective against *Candida albicans* a common causative agent of onychomycosis.

Example 4: Cytotoxicity Evaluation

The study was conducted to assess the biological reactivity of mammalian cells (grown in culture) to the agar-diffusible elements of Formulation 1.

The samples to be evaluated for cytotoxicity include test product comprising Formulation 1, Amber latex tubing as a positive control, and HDPE sheet stock as a negative control. The samples were sized to have no less than 100 mm² of contact surface and provide coverage of approximately 10% of the test dish. The dimensions of the test product comprising Formulation 1 were 1.1×1.1-1.2 cm; the dimensions of the positive control were 1.0×2.55-2.7 cm; and the dimensions of the negative control were 1.15×1.0-1.2 cm. The manipulation of the samples was performed aseptically.

Prior to exposure to the samples, the L929 Mouse Fibroblast cells were subcultured in Minimum Essential Medium (MEM) with 10% Fetal Bovine Serum (FBS) to achieve a confluency of approximately 80±10% at the time of exposure. The cells were examined for normal morphology and the absence of contamination. Once the cells met the acceptance criteria for use, individual dishes were numbered in triplicate to represent the controls and the test product comprising Formulation 1.

On the day of testing, the subculture media was carefully removed from each test dish and replaced with a 2 mL aliquot of the 1:1 overlay medium (in equal parts of 2× Minimum Essential Medium (with 2% Fetal Bovine Serum) and Agar Noble). After allowing the overlay medium to solidify, a single test product comprising Formulation 1 or control sample was placed in the center of each dish (in contact with the agar surface). Triplicate cultures were prepared for each test product comprising Formulation 1 and positive and negative controls (one sample per dish). When the test product comprising Formulation 1 or positive/negative control has only one face designated for patient-contact, that "side" of the sample was directed toward the agar. The test dishes, along with 3 dishes with overlay medium only (Monolayer Negative Controls), were then placed in the 37° C./5% $CO_2$ incubator to initiate the exposure interval.

The dishes were incubated for 24 hours and then microscopically examined for an indication of cellular response. A preliminary microscopic examination of the cells was made prior to staining and before the control and test product comprising Formulation 1 were removed from the agar layer. The cells were then stained with a fresh working Neutral Red Solution to facilitate response grading. The test product comprising Formulation 1 and control samples were removed from the dishes at this time. The stained cells were then fixed by the addition of buffered formalin. Following fixation, the agar overall was removed from each dish. Following staining, the cellular responses were then evaluated microscopically and macroscopically (by examining the dishes against a white surface) and the results were recorded.

For the control samples to be deemed valid, the negative controls may be no greater than Grade 0 and the positive control may be no less than Grade 3. For the test product comprising Formulation 1, a Grade of 0, 1 (slight) or 2 (mild) indicates the test product comprising Formulation 1 "meets" the assay acceptance criteria and a Grade of 3 (moderate) or 4 (severe) indicates the test product comprising Formulation 1 does not meet the assay acceptance criteria. Table 6 depicts the Grading guidelines.

TABLE 6

Grading Guidelines.

| Grade(1) | Reactivity | Description of the Reactivity Zone(2) |
|---|---|---|
| 0 | None | No detectable zone around or under specimen |
| 1 | Slight | Some malformed or degenerated cells under specimen(3) |
| 2 | Mild | Zone limited to area under specimen |
| 3 | Moderate | Zone extends 0.45 to 1.0 cm beyond specimen |
| 4 | Severe | Zone extends greater than 1.0 cm beyond specimen |

(1)The use of the above Grading Table is contingent on the test article meeting the minimum surface area requirements of ≥100 mm². Should samples of smaller dimensions be tested, the reactivity (if any) would be expected to be less and the grading would need to be justified.
(2)The extent of the Reactivity Zone is the maximum measured distance from the edge of the specimen to the margin of monolayer where degenerated cells are no longer observed. Where described as "under specimen", this maximum measured distance is limited to <0.45 cm beyond the specimen.
(3)To be interpreted as "slight" reactivity, no more than 50% of the cells under the specimen may exhibit reactivity as rounding and/or lysis.

Table 7 depicts the results of the study. The assay controls met the acceptance criteria for a valid assay. All negative controls responses were no greater than Grade 0 and the positive control response were not less than Grade 3. The responses observed for the test product comprising Formulation 1 were interpreted according to the current USP guidelines. The Grade 1 response from the test product comprising Formulation 1 is considered to be "non-cytotoxic" (i.e. meets ISO test acceptance requirements of no more than Grade 2 reactivity). Accordingly, Formulation 1 does not damage mammalian cells.

TABLE 7

Study Results.

| | Macroscopic Reading (Zone Dimensions) | | Microscopic Reading (% Rounded/Lysed) | Grade |
|---|---|---|---|---|
| Monolayer Negative Control | 1 | No detectable zone | 0%/0% | 0 |
| | 2 | No detectable zone | 0%/0% | 0 |
| | 3 | No detectable zone | 0%/0% | 0 |
| Material Positive Control | 1 | Clear Zone 3.2 × 3.2; Greatest distance from specimen 1.5 cm | 100%/100% | 4 |
| | 2 | Clear Zone 3.2 × 3.2; Greatest distance from specimen 1.5 cm | 100%/100% | 4 |
| | 3 | Clear Zone 3.2 × 3.2; Greatest distance from specimen 1.5 cm | 100%/100% | 4 |
| Material Negative | 1 | No detectable zone | 0%/0% | 0 |
| | 2 | No detectable zone | 0%/0% | 0 |

TABLE 7-continued

Study Results.

| | Macroscopic Reading (Zone Dimensions) | | Microscopic Reading (% Rounded/Lysed) | Grade |
|---|---|---|---|---|
| Control | 3 | No detectable zone | 0%/0% | 0 |
| Test Product Comprising Formulation 1 | 1 | Entire dish lightly stained ~5% rounded directly under sample | 1.5%/1.5% | 1 |
| | 2 | Entire dish lightly stained ~5% rounded directly under sample | 1.5%/1.5% | 1 |
| | 3 | Entire dish lightly stained ~5% rounded directly under sample | 1.5%/1.5% | 1 |

Example 5: Rabbit Skin Irritation

The study was conducted to assess the irritating potential of Formulation 1 to produce dermal irritation.

Figure 4:
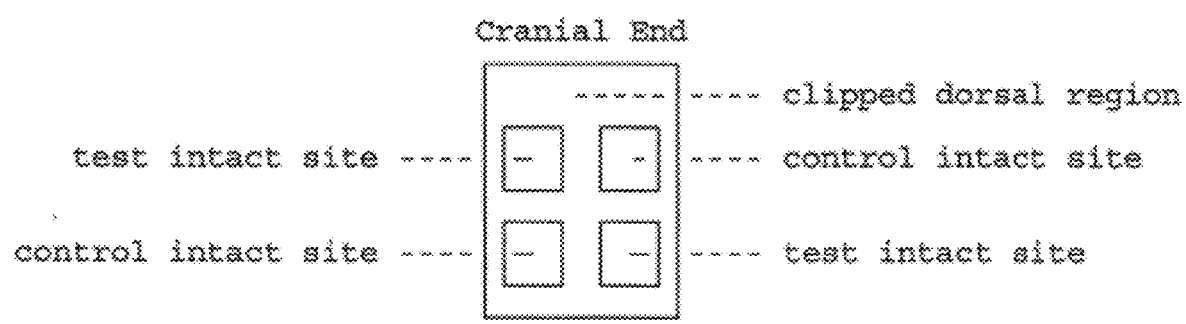
FIG. 4 depicts a schematic of the arrangement of test and control sites in the rabbit skin irritation study, according to an exemplary embodiment of the present disclosure.

Within 24 hours to 4 hours before test application, the backs of female albino New Zealand White rabbits were clipped free of hair, exposing 2 test and 2 control areas on each side of the spine with a size of approximately 15 cm×15 cm. The two test sites are located on the left cranial section and the right caudal section of the dorsal region. The two control sites are located on the left caudal and right cranial section of the dorsal region. FIG. 4 depicts the arrangement of test and control sites. The exposed skin is wiped with alcohol and dried. Rabbits of acceptable skin quality were selected and used for testing.

A 25×25 mm gauze patch saturated with 0.5 mL (liquid) or 0.5 g (powder) of Formulation 1 is applied to the clipped test sites. A 25×25 mm gauze patch saturated with 0.5 mL of 0.9% NaCl is used for the control and applied to the clipped control sites. The patches are secured using hypoallergenic, waterproof, surgical tape over the test and control sites. The animal's trunk is securely wrapped so as to maintain the position of the patches. Patches are left applied for a minimum of four hours.

After patch removal, the test and control sites were then scored for erythema and edema at 1, 24, 48 and 72 hours after patch removal. Only the 24, 48, and 72 hour observations were scored and used for calculations. The criteria for scoring is presented in Table 8. If no response was expected, testing was conducted using three animals per test article. If irritation was anticipated, one animal was tested initially. If the first animal received a score of 2 or less for either erythema or edema, 2 additional rabbits were used to conclude the test.

TABLE 8

Scoring Criteria for Test Reactions.

| Reaction | Description | Score |
|---|---|---|
| Erythema (ER) | No erythema | 0 |
| | Very slight (barely perceptible) | 1 |
| | Well defined | 2 |
| | Moderate | 3 |
| | Severe (beet-redness) to eschar formation preventing grading of erythema | 4 |

TABLE 8-continued

Scoring Criteria for Test Reactions.

| Reaction | Description | Score |
|---|---|---|
| Edema | No edema | 0 |
| (ED) | Very slight (barely perceptible) | 1 |
| | Well-defined edema (edges of area well-defined by definite raising | 2 |
| | Moderate (edges raised ~1 mm) | 3 |
| | Severe (raised more than 1 mm and extending beyond exposure area) | 4 |

For each animal and each extract, when applicable, the scores for the test article comprising Formulation 1 for erythema and edema at each time were added. This total was divided by the total number of observations. The same was done for the control sites. The control result was subtracted from the test results to give the irritation index for each animal. These scores for each animal were added and divided by the total number of animals to give the Primary Irritation Index. The Primary Irritation Index is depicted in Table 9. For any response, the Maximum Irritation Response, the time of onset of the response and the time of maximum response was recorded.

TABLE 9

Primary Irritation Index

| Primary Irritation Index | Response Category |
|---|---|
| 0-0.4 | Negligible |
| 0.5-1.9 | Slight |
| 2-4.9 | Moderate |
| 5-8 | Severe |

The results indicated that the skin reactions for both the test article comprising Formulation 1 and control samples were not significant. That data is presented in Table 10 below. Accordingly, the Formulation 1 is non-irritating.

TABLE 10

Direct Application of Test Article.

| | Formulation 1 | | | Control | | |
|---|---|---|---|---|---|---|
| Rabbit No. 14384 | ER + ED = Total | | | ER + ED = Total | | |
| | 0 | 0 | 0 | 0 | 0 | 0 |
| | Test Total-Control Total = 0 | | | | | |
| | Total Score Average = 0 | | | | | |
| Rabbit No. 14387 | ER + ED = Total | | | ER + ED = Total | | |
| | 0 | 0 | 0 | 0 | 0 | 0 |
| | Test Total-Control Total = 0 | | | | | |
| | Total Score Average = 0 | | | | | |
| Rabbit No. 14394 | ER + ED = Total | | | ER + ED = Total | | |
| | 0 | 0 | 0 | 0 | 0 | 0 |
| | Test Total-Control Total = 0 | | | | | |
| | Total Score Average = 0 | | | | | |

Total Average (0) = 0 Primary Irritation Index
No. of Animals (3)

To positively validate the test, 10% sodium dodecyl sulfate (SDS), which is a known dermal irritant, in petroleum jelly was applied to a 2.5 cm×2.5 cm gauze patch. As a negative control, 0.5 mL of 0.9% NaCl was applied to a 2.5 cm×2.5 cm gauze patch. A Primary Irritation Index in the moderate to severe range is considered a positive result. The test system and methods utilized were the same as described above. Table 11 presents the results validating the study.

TABLE 11

Primary Skin Positive Validation Test.

| | 10% SDS | | | Control | | |
|---|---|---|---|---|---|---|
| Rabbit No. 14279 | ER + ED = Total | | | ER + ED = Total | | |
| | 18 | 14 | 32 | 0 | 0 | 0 |
| | Test Total-Control Total = 32 | | | | | |
| | Total Score Average = 5.3 | | | | | |
| Rabbit No. 14280 | ER + ED = Total | | | ER + ED = Total | | |
| | 21 | 19 | 40 | 0 | 0 | 0 |
| | Test Total-Control Total = 40 | | | | | |
| | Total Score Average = 6.6 | | | | | |
| Rabbit No. 14281 | ER + ED = Total | | | ER + ED = Total | | |
| | 23 | 21 | 44 | 0 | 0 | 0 |
| | Test Total-Control Total = 44 | | | | | |
| | Total Score Average = 7.3 | | | | | |

Total Average (19.3) = 6.4 Primary Irritation Index
No. of Animals (3)

Example 6. Suspension Time-Kill Procedure for MRSA, *T. rubrum*, and *Staphylococcus epidermidis*

A study was conducted to evaluate the changes in the population of MRSA in an antimicrobial liquid suspension comprising Formulation 1. Methicillin-resistant *Staphylococcus aureus* (MRSA) is a Gram-positive, cocci shaped, aerobe which is resistant to the penicillin-derivative antibiotic methicillin. MRSA can cause troublesome infections, and their rapid reproduction and resistance to antibiotics makes them more difficult to treat. MRSA bacteria are resistant to drying and can therefore survive on surfaces and fabrics for an extended period of time and therefore makes this bacteria an excellent representative for antimicrobial efficacy testing on surfaces.

Figure 5:
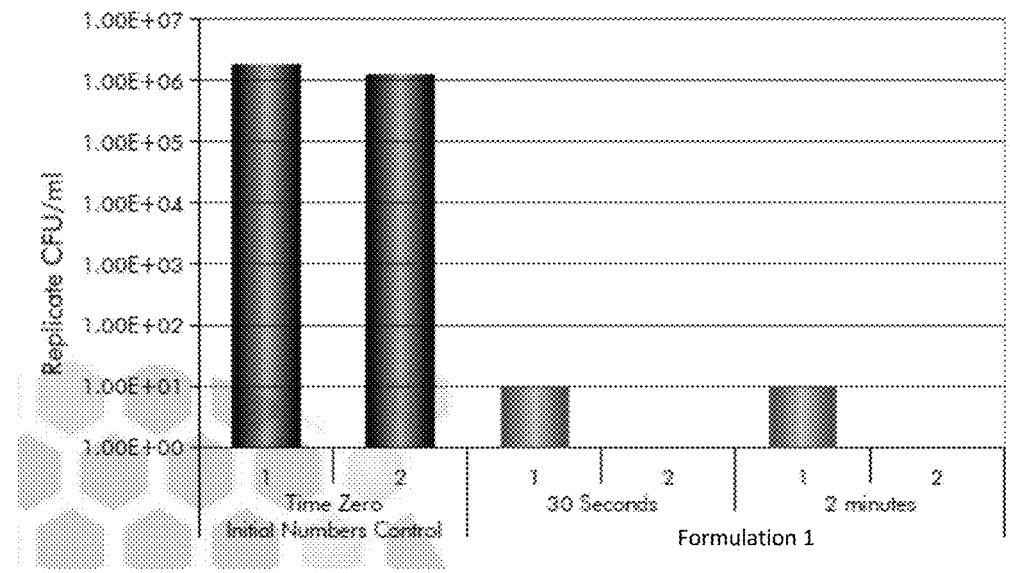
FIG. 5 depicts a graph showing the reduction of MRSA in the presence of Formulation 1 in the suspension time-kill procedure, according to an exemplary embodiment of the present disclosure.

To conduct the study, MRSA was prepared in liquid culture medium (Letheen Broth). The suspension of MRSA was standardized by dilution to $10^6$ in a buffered saline solution. Formulation 1 and control substance (PBS) were dispensed in identical volumes to sterile vessels. Independently, Formulation 1 and control substance were each inoculated with MRSA, then mixed and incubated. Control substances were immediately harvested and represented the concentration present at the start at the test (i.e. time zero). At the conclusion of contact time, a volume of the liquid test product was harvested and chemically neutralized. Dilutions of the neutralized test solution were assayed using appropriate growth media to determine the surviving MRSA at the respective contact times. Reductions in MRSA were calculated by comparing initial microbial concentrations to final microbial concentrations. Table 12 and FIG. 5 present the results of the study.

TABLE 12

Results of Suspension Time-Kill Test for MRSA (33592)

| Test substance | Contact time | Replicate | Replicate CFU/ml* | Average CFU/ml | Percent Reduction vs. Control at Time Zero | $Log_{10}$ Reduction vs. Control at Time Zero |
|---|---|---|---|---|---|---|
| PBS | Time Zero | 1 | 1.75E+06 | 1.48E+06 | N/A | |
| | | 2 | 1.20E+06 | | | |
| Formulation 1 | 30 seconds | 1 | 1.00E+01 | <1.00E+01 | >99.9993% | >5.17 |
| | | 2 | <1.00E+01 | | | |
| | 2 minutes | 1 | 1.00E+01 | <1.00E+01 | >99.9993% | >5.17 |
| | | 2 | <1.00E+01 | | | |

*The limit of detection for the assay is 1.00E+01 CFU/ml. Values below the limit of detection are notes as <1.00E+01 in the table.

The same study was conducted with *Trichophyton rubrum*. *T. rubrum* is a fungus which belongs to the dermatophyte group. Dermatophytes commonly cause skin disease in animals and humans. *T. rubrum* is anthropophilic, meaning it preferentially infects humans over animals. This parasite is the most common cause of fungal infection of the fingernail and Athlete's foot, this specific strain was isolated from a human toenail. In the laboratory, visible colonies can be observed after approximately 4-5 days and are fluffy and white in appearance. *T. rubrum* is a popular test microorganism for fungicidal testing, especially for products intended for use in environments where skin infections can occurs and spread rapidly such as locker rooms and schools.

Figure 6:
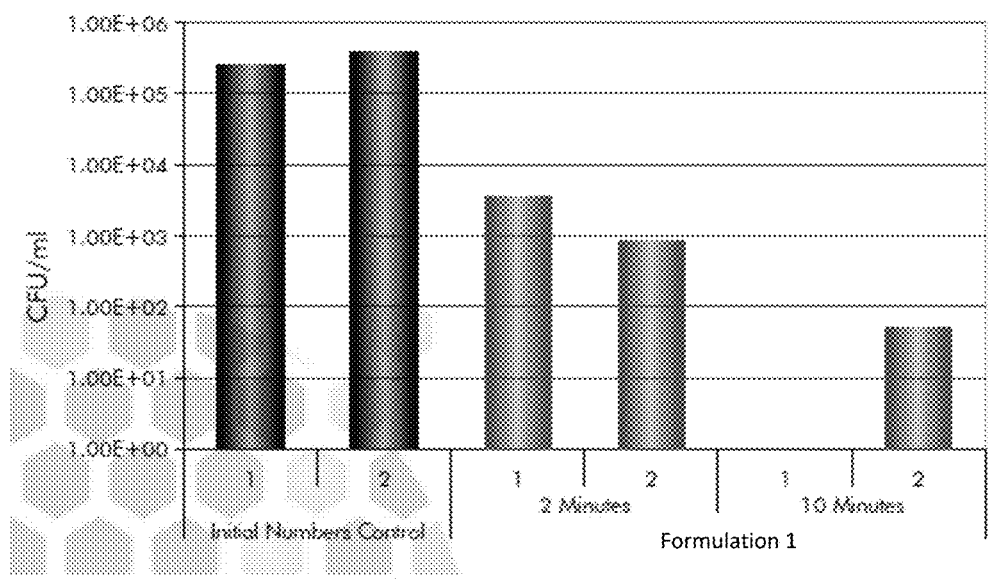
FIG. 6 depicts a graph showing the reduction of *T. rubrum* in the presence of Formulation 1 in the suspension time-kill procedure, according to an exemplary embodiment of the present disclosure.

To conduct the study, *T. rubrum* was prepared on agar (potato dextrose agar). The *T. rubrum* was resuspended and inoculated at a dilution of ~$10^6$ into vessels containing Formulation 1 and control substance (PBS). Control substances were immediately harvested and represented the concentration present at the start at the test (i.e. time zero). At the conclusion of contact time (2 or 10 minutes), a volume of the liquid test product was harvested and chemically neutralized. Dilutions of the neutralized test solution were assayed using appropriate growth media to determine the surviving *T. rubrum* at the respective contact times. Reductions in *T. rubrum* were calculated by comparing initial microbial concentrations to final microbial concentrations. Table 13 and FIG. 6 present the results of the study.

TABLE 13

Results of Suspension Time-Kill Test for *T. rubrum* (MYA-4438)

| Test substance | Contact time | Replicate | Replicate CFU/ml* | Average CFU/ml | Percent Reduction vs. Control at Time Zero | $Log_{10}$ Reduction vs. Control at Time Zero |
|---|---|---|---|---|---|---|
| PBS | Time Zero | 1 | 2.55E+05 | 3.15E+05 | N/A | |
| | | 2 | 3.75E+05 | | | |
| Formulation 1 | 2 minutes | 1 | 3.50E+03 | 2.18E+03 | 99.31% | 2.16 |
| | | 2 | 8.50E+02 | | | |
| | 10 minutes | 1 | <5.00E+01 | <5.00E+01 | >99.98% | >3.80 |
| | | 2 | 5.00E+01 | | | |

*The limit of detection for the assay is 5.00E+01 CFU/ml. Values below the limit of detection are notes as <5.00E+01 in the table.

The same study was conducted with *Staphylococcus epidermidis*. Gram-positive organisms currently account for 50-60% of nosocomial bacteremic events. *Staphylococcus epidermidis* is the most common gram-positive organism isolated from blood (30% of isolates) and accounts for the majority of infections that are associated with intravascular catheters, as it is capable of forming antibiotic resistant biofilms on plastic surfaces.

In an effort to further explore the preventative benefits of Formulation 1 in preventing catheter related and hospital acquired infections, a suspension time kill assay as described above was initiated on this often under-discussed organism. A nearly 7 log kill over 24 hours was observed, which represents a typical change interval for intravenous catheter dressings (Table 14).

TABLE 14

Results of Suspension Time-Kill Test for *S. epidermidis* (ATCC 12228)

| Test substance | Contact time | Replicate CFU/ml* | Percent Reduction vs. Control at Time Zero | $Log_{10}$ Reduction vs. Control at Time Zero |
|---|---|---|---|---|
| PBS | Time Zero | 4.80E+06 | N/A | |
| Formulation 1 | 24 Hours | <1.00E+00 | >99.99998% | >6.68 |

The limit of detection is 1.00E+00 and is represented as <1.00E+00.

Example 6 indicates that the presently disclosed compositions are effective against *Trichophyton rubrum* a common causative agent of onychomycosis. Specifically, after 10 minutes, the Formulation 1 composition of Example 1 reduced *T. rubrum* by more than 99.98%.

Example 7. Stability

Formula I as packaged in tubes was subjected to an accelerated stability study. Formula I was placed sideways in a 40° C.±2° C./75%±5% relative humidity (RH) storage chamber for different intervals to yield a period of three months. The product was assessed for physical and analytical characteristics. When stored at 40° C.±2° C./75%±5% (RH) benzyl alkonium chloride was stable as shown in Table 15.

TABLE 15

Accelerated Stability Testing

| Analytical Assay Testing | Specification | Initial: Assessing | 1 Month Assessing | 2 Months Assessing | 3 Months Assessing |
|---|---|---|---|---|---|
| Benzalkonium Chloride 0.0081% | 0.0071%-0.0086% | 0.0084% | 0.0085% | 0.0075% | 0.0086% |

Additionally, the product met specification for appearance, odor, specific gravity, viscosity and package compatibility at all time points tested.

Formula I was also tested under for microbial counts at 40° C.±2° C./75%±5% were as shown below. The results are shown in Table 16.

TABLE 16

| Micro Testing | SPEC | Method | Results Initial Assessing | 1 Month Assessing | 2 Months Assessing | 3 Months Assessing |
|---|---|---|---|---|---|---|
| Total Place Count (TPC) | <100 cfu/ml | TM-01 | <10 cfu/ml | <10 cfu/ml | <10 cfu/ml | <10 cfu/ml |
| Yeast/Mold | <100 cfu/ml | TM-01 | <10 cfu/ml | <10 cfu/ml | <10 cfu/ml | <10 cfu/ml |
| Enrichment (Pathogens) | Absent | Absent | Absent | Absent | Absent | Absent |
| Pseudomonas | Absent | Absent | Absent | Absent | Absent | Absent |
| S. aureus | Absent | Absent | Absent | Absent | Absent | Absent |
| E. coli | Absent | Absent | Absent | Absent | Absent | Absent |
| Coliforms | Absent | Absent | Absent | Absent | Absent | Absent |
| Salmonella/Shigella | Absent | Absent | Absent | Absent | Absent | Absent |

Additionally, the product met specification for appearance, odor, specific gravity, viscosity and package compatibility at all time-points tested when under standard conditions for over nine months.

Example 8. Formulation Example 1

A petrolatum-based composition in accordance with the present disclosure was prepared by mixing 1000 cc of water containing 2% by weight PHMB and 0.13% by weight BZK. The water solution was heated to 40° C. and was then added to 19,000 cc of petrolatum at about 45° C. to give 20,000 cc of a petrolatum-based composition containing BZK and PHMB.

Example 9. Formulation Example 2

A petrolatum-based composition in accordance with the present disclosure was prepared by mixing 1000 cc of water containing 2% by weight PHMB. This solution was then added to 20,000 cc of petrolatum to give 21,000 cc of a petrolatum-based composition containing PHMB Example 10. Formulation Example 3

A petrolatum-based composition in accordance with the present disclosure was prepared by mixing PHMB, BZK and water to form a PHMB solution that contained 10% by weight PHMB, 0.13% by weight BZK, and 89.87% by weight water. The PHMB solution was heated to a temperature from about 1° C. to about 5° C. higher than the temperature of the melted petrolatum and mixed to form a composition comprising 95% by weight petrolatum, 4.4935% by weight water, 0.5% by weight PHMB, and 0.0065% by weight BZK.

Example 11. Formulation Example 4

A petrolatum-based composition in accordance with the present disclosure was prepared by mixing 100 mL of a 20% PHMB solution, 162.5 mL of a 80% BZK solution, and 737.5 mL of water to form 1000 mL of a PHMB solution. Separately, 1900 mL of petrolatum was heated to a temperature sufficient to completely melt the petrolatum and left at that temperature. The 1000 mL PHMB solution was then heated to a temperature from about 1° C. to about 5° C. higher than the temperature of the melted petrolatum and mixed with the 19000 mL heated petrolatum and stirred to form a melted mixture of PHMB and petrolatum. The melted mixture was then allowed to cool to room temperature to form the petrolatum-based PHMB composition.

Example 12. Formulation Example 5

A petrolatum-based composition in accordance with the present disclosure was prepared by mixing 100 mL of a 20% PHMB solution, 162.5 mL of a 80% BZK solution, 100 mL of ethanol, and 637.5 mL of water to form 1000 mL of a PHMB solution. Separately, 1900 mL of petrolatum was heated to a temperature sufficient to completely melt the petrolatum and left at that temperature. The 1000 mL PHMB solution was then heated to a temperature from about 1° C. to about 5° C. higher than the temperature of the melted petrolatum and mixed with the 19000 mL heated petrolatum and stirred to form a melted mixture of PHMB and petrolatum. The melted mixture was then allowed to cool to room temperature to form the petrolatum-based PHMB composition.

Example 13. Formulation Example 6

A petrolatum-based composition in accordance with the present disclosure was prepared by mixing 100 mL of a 20% PHMB solution, 162.5 mL of a 80% BZK solution, 200 mL ethanol, and 537.5 mL of water to form 1000 mL of a PHMB solution. Separately, 1900 mL of petrolatum was heated to a temperature sufficient to completely melt the petrolatum and left at that temperature. The 1000 mL PHMB solution was then heated to a temperature from about 1° C. to about 5° C. higher than the temperature of the melted petrolatum and mixed with the 19000 mL heated petrolatum and stirred to form a melted mixture of PHMB and petrolatum. The melted mixture was then allowed to cool to room temperature to form the petrolatum-based PHMB composition.

Example 14. Efficacy of Formulation 1 of Example 1 on *Candida auris* (*C. auris*) CDC AR Bank #0381

*Candida auris* is an emerging fungus which presents a serious global health threat according to the Centers for Disease Control and Prevention (CDC). *C. auris* is one of the few species of the *Candida* genus which cause candidiasis in humans. Although *C. auris* was not described until 2009 and does not appear to have been previously a common colonizer of humans, *C. auris* is quickly becoming more common. For example, within just a few years in some international healthcare facilities, *C. auris* has emerged from being a relatively unknown pathogen to the cause of 40% of invasive *Candida* infections. *C. auris* can spread between patients in healthcare facilities and cause outbreaks. *C. auris* is frequently multidrug-resistant and can colonize a patient's skin for months or longer. *C. auris* can also live on surfaces for a month or more and conventional healthcare disinfection techniques appear to be inadequate in controlling *C. auris* in at least some instances. In some cases, the onychomycosis may be caused by *C. auris*.

A study was conducted on the formulation of Example 1, referred to herein as "Formulation 1" to assess efficacy to treat or control *C. auris*. In particular, ASTM International Standard Test Method E1153 was used as a quantitative test method to assess the antimicrobial effectiveness of Formulation 1 as a sanitizer on pre-cleaned inanimate, non-porous, non-food contact surfaces. In the ASTM E1153 test, *C. auris* CDC AR Bank #0381 test organism was cultured to produce a test culture. Sterilized carriers were inoculated with a volume of the test culture and inoculated slides were dried in an incubator. Only completely dried carriers were used in the test. Control carriers were harvested following the dry time to determining the initial inoculation concentration. Test carriers were treated with the test substance and incubated for the predetermined contact time. At the conclusion of the contact time, test carriers were chemically neutralized. Dilutions of the neutralized test substance were evaluated using appropriate growth media to determine the surviving microorganisms at the respective contact time. The effect of the test substance was compared to the effect of the control substance in order to determine microbial reductions.

Figure 7:
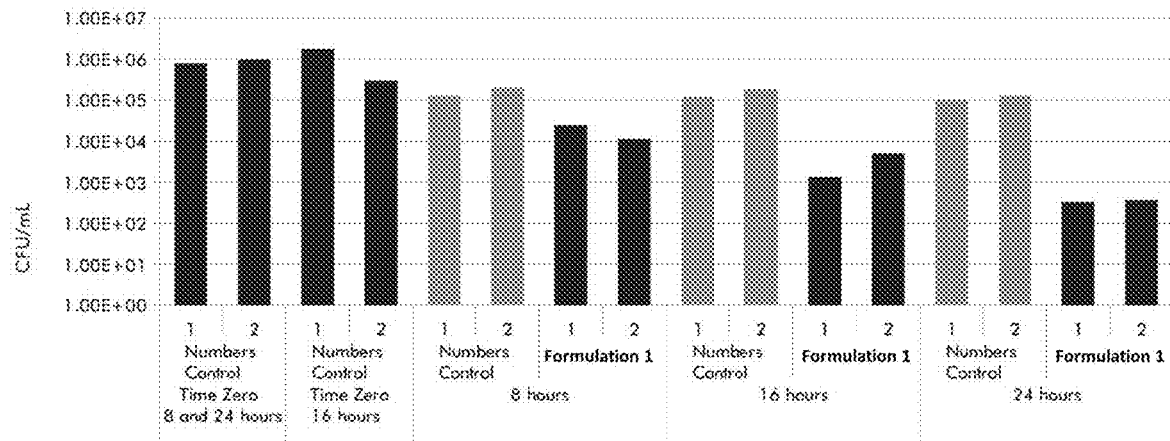
FIG. 7 depicts a graph showing the reduction of *C. auris* CDC AR Bank #0381 test microorganisms according to a modified ASTM International Method E1153 test following administration of Formulation 1 of Example 1, according to an exemplary embodiment of the present disclosure.

The results of the test are shown in Tables 17 and 18 and FIG. 7. The Percent reduction was determined according to the following formula:

$$\text{Percent Reduction} = \left(\frac{B-A}{B}\right) \times 100,$$

where B equals the number of viable test microorganisms on the control carriers after the contact time and A equals the number of viable test microorganisms on the test carriers after the contact time. Log 10Reduction was calculated according to the following formula:

$$\text{Log}_{10}\text{Reduction} = \text{Log}\left(\frac{B}{A}\right),$$

where B equals the number of viable test microorganisms on the control carriers after the contact time and A equals the number of viable test microorganisms on the test carriers after the contact time. As shown in Tables 17 and 18 and FIG. 7, Formulation 1 is effective in killing *C. auris* CDC AR Bank #0381 under the conditions of the test. As a result, it is expected that Formulation 1 is effective in the treatment and control of *C. auris* on nail surfaces including the nail plate, nail bed, and on other surfaces adjacent to the nail.

TABLE 17

Efficacy of Formulation 1 (Example 1) Against *C. auris* CDC AR Bank #0381

| Contact Times | Test Substance | Replicate | CFU/carrier | Average CFU/carrier | Percent Reduction Compared to Control at Contact Time | Log$_{10}$ Reduction Compared to Control at Contact Time |
|---|---|---|---|---|---|---|
| Time Zero 8 and 24 hours | Numbers Control | 1 | 7.40E+05 | 8.20E+05 | N/A | |
| | | 2 | 9.00E+05 | | | |
| Time Zero 16 hours | Numbers Control | 1 | 1.63E+06 | 9.55E+05 | N/A | |
| | | 2 | 2.80E+05 | | | |
| 8 hour | Numbers Control | 1 | 1.24E+05 | 1.55E+05 | N/A | N/A |
| | | 2 | 1.85E+05 | | | |
| | Formulation 1 | 1 | 2.40E+04 | 1.75E+04 | 88.67% | 0.95 |
| | | 2 | 1.10E+04 | | | |
| 16 hours | Numbers Control | 1 | 1.17E+05 | 1.49E+05 | N/A | N/A |
| | | 2 | 1.81E+05 | | | |
| | Formulation 1 | 1 | 1.29E+03 | 3.19E+03 | 97.86% | 1.67 |
| | | 2 | 5.08E+03 | | | |
| 24 hours | Numbers Control | 1 | 9.90E+04 | 1.10E+05 | N/A | N/A |
| | | 2 | 1.20E+05 | | | |
| | Formulation 1 | 1 | 3.20E+02 | 3.40E+02 | 99.69% | 2.51 |
| | | 2 | 3.60E+02 | | | |

TABLE 18

Efficacy of Formulation 1 (Example 1) Against *C. auris* CDC AR Bank #0381

| Test Substance | Neutralization Validation Counts (CFU) | Average NV Counts (CFU) | Percent Difference | Result |
|---|---|---|---|---|
| Control | 77/84 | 80.5 | 83.85% | Verified |
| Formulation 1 | 67/68 | 67.5 | | |

Example 15. Efficacy of Formulation 1 of Example 1 on *Candida auris* (*C. auris*) CDC AR Bank #0381 Inoculated Vitro Skin A study was conducted on the formulation of Example 1, referred to herein as "Formulation 1" to assess efficacy to treat or control *C. auris* on skin. In particular, ASTM International Standard Test Method E1153 was used as a quantitative test method to assess the antimicrobial effectiveness of Formulation 1 on inoculated vitro skin that was incubated at body temperature (37° C.). In the ASTM E1153 test, *C. auris* CDC AR Bank #0381 test organism was cultured to produce a test culture. Vitro skin carriers were inoculated with a volume of the test culture and inoculated vitro skin was incubated at 37° C. Control carriers were harvested following the incubation period to determine the initial inoculation concentration. Test vitro skin carriers were treated with the test substance and incubated at 37° C. for the predetermined contact time. At the conclusion of the contact time, test vitro skin carriers were chemically neutralized. Dilutions of the neutralized test substance were evaluated using appropriate growth media to determine the surviving microorganisms at the respective contact time. The effect of the test substance was compared to the effect of the control substance in order to determine microbial reductions.

The results of the test are shown in Table 19. The Percent reduction was determined according to the following formula:

$$\text{Percent Reduction} = \left(\frac{B-A}{B}\right) \times 100,$$

where B equals the number of viable test microorganisms on the control carriers after the contact time and A equals the number of viable test microorganisms on the test carriers after the contact time. Log 10Reduction was calculated according to the following formula:

$$\text{Log}_{10}\text{Reduction} = \text{Log}\left(\frac{B}{A}\right),$$

where B equals the number of viable test microorganisms on the control carriers after the contact time and A equals the number of viable test microorganisms on the test carriers after the contact time. As shown in Table 19, Formulation 1 is effective in killing *C. auris* AR Bank #0381 under the conditions of the vitro skin test. As a result, it is expected that Formulation 1 is effective in the treatment and control of *C. auris* on nail surfaces including the nail plate, nail bed, and on other surfaces adjacent to the nail.

TABLE 19

Efficacy of Formulation 1 (Example 1) Against *C. auris* CDC AR Bank #0381

| Contact Times | Test Substance | Replicate | CFU/carrier | Average CFU/carrier | Percent Reduction Compared to Control at Contact Time | Log$_{10}$ Reduction Compared to Control at Contact Time |
|---|---|---|---|---|---|---|
| Time Zero | Numbers Control | 1 | 9.00E+05 | 1.07E+06 | N/A | |
| | | 2 | 1.24E+06 | | | |
| 8 hours | Formulation 1 | 1 | 2.25E+05 | 2.21E+05 | 79.35% | 0.7 |
| | | 2 | 2.17E+05 | | | |
| 16 hours | Formulation 1 | 1 | 1.82E+04 | 1.56E+04 | 98.54% | 1.8 |
| | | 2 | 1.30E+04 | | | |
| 24 hours | Numbers Control | 1 | 1.17E+06 | 9.50E+05 | N/A | N/A |
| | | 2 | 7.30E+05 | | | |
| | Formulation 1 | 1 | 1.21E+05 | 9.50E+04 | 91.12% | 1.05 |
| | | 2 | 6.90E+04 | | | |

Example 16. Efficacy of Formulation 1 of Example 1 on *Candida auris* (*C. auris*) CDC AR Bank #0381

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0381 test organism was cultured to produce a test culture. The suspension of test microorganisms was standardized, as needed, by dilution in a buffered saline solution. Test and control substances were dispensed in identical volumes to sterile vessels. 10 grams of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration plates were incubated for 72-120 hours. No additional growth or re-colonization was observed after this period.

Figure 8:
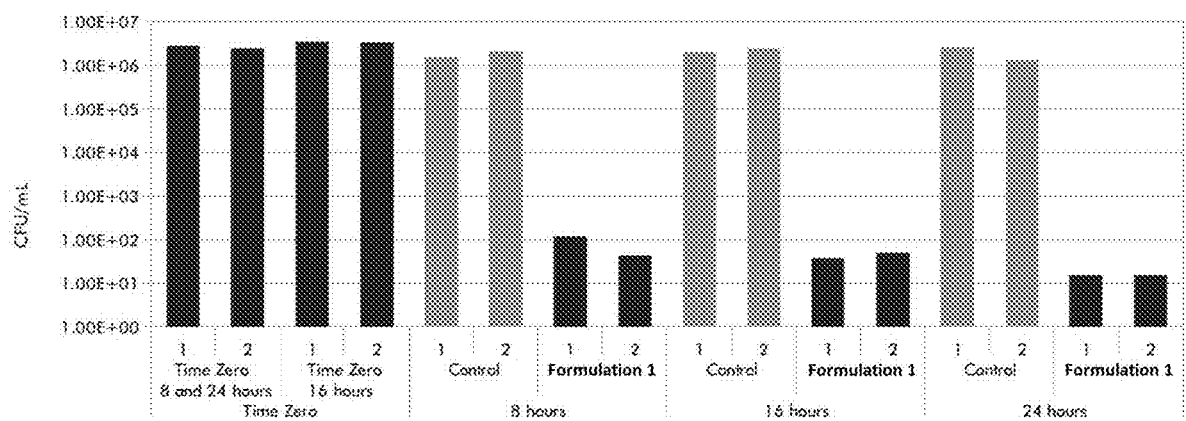
FIG. 8 depicts a graph showing the reduction of *C. auris* CDC AR Bank #0381 test microorganisms according to a ASTM International Method E2315 test following administration of Formulation 1 of Example 1, according to an exemplary embodiment of the present disclosure.

The results of the test are shown in Table 20 and FIG. 8. The Percent reduction was determined according to the following formula:

$$\text{Percent Reduction} = \left(\frac{B-A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$\text{Log}_{10}\text{Reduction} = \text{Log}\left(\frac{B}{A}\right),$$

where B equals the number of viable test microorganisms in the control substance immediately after inoculation and A equals the number of viable test microorganisms in the test substance after the contact time. As shown in Table 20 and FIG. 8, Formulation 1 is effective in killing *C. auris* AR Bank #0381 under the conditions of the test. As a result, it is expected that Formulation 1 is effective in the treatment and control of *C. auris* on nail surfaces including the nail plate, nail bed, and on other surfaces adjacent to the nail.

TABLE 20

Efficacy of Formulation 1 (Example 1) Against *C. auris* CDC AR #0381

| Contact Times | Test Substance | Replicate | CFU/mL | Average CFU/mL | Percent Reduction Compared to Control at Contact Time | Log$_{10}$ Reduction Compared to Control at Contact Time |
|---|---|---|---|---|---|---|
| Time Zero | Numbers Control for 8 and 24 hours | 1 | 2.65E+06 | 2.50E+06 | N/A | |
|  |  | 2 | 2.35E+06 |  |  |  |
|  | Numbers Control for 16 hours | 1 | 3.35E+06 | 3.25E+06 | N/A | |
|  |  | 2 | 3.15E+06 |  |  |  |
| 8 hours | Numbers Control | 1 | 1.45E+06 | 1.74E+06 | N/A | |
|  |  | 2 | 2.02E+06 |  | N/A | |
|  | Formulation 1 | 1 | 1.20E+02 | 8.00E+01 | 99.995% | 4.34 |
|  |  | 2 | 4.00E+01 |  |  |  |
| 16 hours | Numbers Control | 1 | 1.97E+06 | 2.16E+06 | N/A | |
|  |  | 2 | 2.35E+06 |  |  |  |
|  | Formulation 1 | 1 | 3.50E+01 | 4.25E+01 | 99.998% | 4.71 |
|  |  | 2 | 5.00E+01 |  |  |  |
| 24 hours | Numbers Control | 1 | 2.42E+06 | 1.84E+06 | N/A | |
|  |  | 2 | 1.26E+06 |  |  |  |
|  | Formulation 1 | 1 | 1.50E+01 | 1.50E+01 | 99.9992% | 5.09 |
|  |  | 2 | 1.50E+01 |  |  |  |

Example 17. Efficacy of Formulation 1 of Example 1 on *Candida auris* (*C. auris*) CDC AR Bank #0384

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0384 test organism was cultured to produce a test culture. The suspension of test microorganisms was standardized, as needed, by dilution in a buffered saline solution. Test and control substances were dispensed in identical volumes to sterile vessels. 1 gram of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration of plates was performed after ~48 hours incubation. No additional growth or re-colonization was observed after this period.

Figure 9:
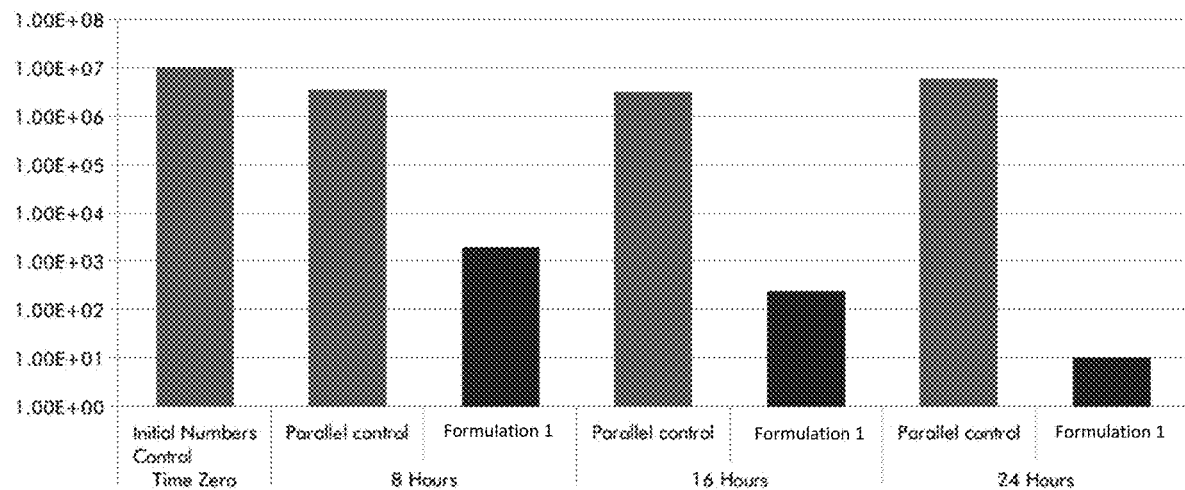
FIG. 9 depicts a graph showing the reduction of *C. auris* CDC AR Bank #0384 test microorganisms according to a ASTM International Method E2315 test following administration of Formulation 1 of Example 1, according to an exemplary embodiment of the present disclosure.

The control substance was phosphate-buffered saline (PBS). The culture growth media and plating media used was potato dextrose agar and the culture dilution media used was PBS. The inoculum concentration was >1.0×10$^6$ CFU/mL and the contact time was 8, 16, and 24 hours. 9 mL of D/E broth was used as the neutralizer. The contact temperature was ~25° C.±2° C. (ambient) and the enumeration plate incubation temperature was 28° C.±2° C. The inoculum volume was 0.100 mL and the volume harvested was 1.0 mL The results of the test are shown in Table 21 and FIG. 9. The Percent reduction was determined according to the following formula:

$$\text{Percent Reduction} = \left(\frac{B-A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$\text{Log}_{10}\text{Reduction} = \text{Log}\left(\frac{B}{A}\right),$$

where B equals the number of viable test microorganisms in the control substance immediately after inoculation and A equals the number of viable test microorganisms in the test substance after the contact time. As shown in Table 21 and FIG. 9, Formulation 1 is effective in killing *C. auris* CDC AR Bank #0384 under the conditions of the test. As a result, it is expected that Formulation 1 is effective in the treatment and control of *C. auris* on nail surfaces including the nail plate, nail bed, and on other surfaces adjacent to the nail.

TABLE 21

Efficacy of Formulation 1 (Example 1) Against *C. auris* CDC AR Bank #0384

| Contact Time | Test Substance | CFU/mL | Percent Reduction vs. Parallel Time Control | Log$_{10}$ Reduction vs. Parallel Time Control |
|---|---|---|---|---|
| Time Zero | Initial Numbers Control | 1.03E+07 | N/A | |
| 8 hours | Parallel Control | 3.50E+06 | N/A | |
|  | Formulation 1 | 1.88E+03 | 99.946% | 3.27 |
| 16 hours | Parallel Control | 3.05E+06 | N/A | |
|  | Formulation 1 | 2.30E+02 | 99.992% | 4.12 |
| 24 hours | Parallel Control | 5.75E+06 | N/A | |
|  | Formulation 1 | <1.00E+01 | 99.99983% | >5.76 |

Example 18. Efficacy of Formulation 1 of Example 1 on *Candida auris* (*C. auris*) CDC AR Bank #0385

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0385 test organism was cultured to produce a test culture. The suspension of test microorganisms was standardized, as needed, by dilution in a buffered saline solution. Test and control substances were dispensed in identical volumes to sterile vessels. 1 gram of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration of plates was performed after ~48 hours incubation. No additional growth or re-colonization was observed after this period.

Figure 10:
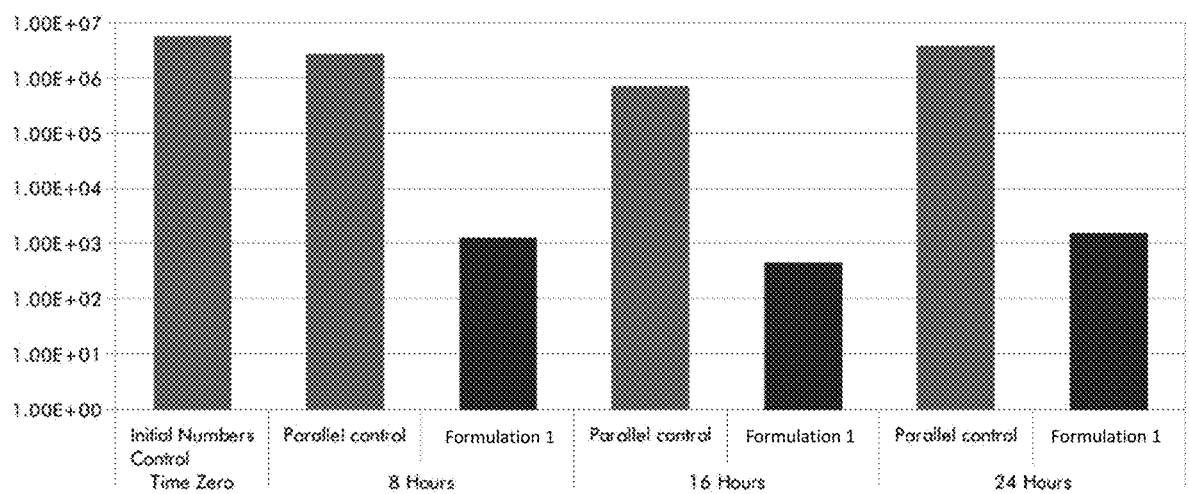
FIG. 10 depicts a graph showing the reduction of *C. auris* CDC AR Bank #0385 test microorganisms according to a ASTM International Method E2315 test following administration of Formulation 1 of Example 1, according to an exemplary embodiment of the present disclosure.

The control substance was phosphate-buffered saline (PBS). The culture growth media and plating media used was potato dextrose agar and the culture dilution media used was PBS. The inoculum concentration was >1.0×10$^6$ CFU/mL and the contact time was 8, 16, and 24 hours. 9 mL of D/E broth was used as the neutralizer. The contact temperature was ~25° C.±2° C. (ambient) and the enumeration plate incubation temperature was 28° C.±2° C. The inoculum volume was 0.100 mL and the volume harvested was 1.0 mL The results of the test are shown in Table 22 and FIG. 10. The Percent reduction was determined according to the following formula:

$$\text{Percent Reduction} = \left(\frac{B-A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$\text{Log}_{10}\text{Reduction} = \text{Log}\left(\frac{B}{A}\right),$$

where B equals the number of viable test microorganisms in the control substance immediately after inoculation and A equals the number of viable test microorganisms in the test substance after the contact time. As shown in Table 22 and FIG. 10, Formulation 1 is effective in killing *C. auris* CDC AR Bank #0385 under the conditions of the test. As a result, it is expected that Formulation 1 is effective in the treatment and control of *C. auris* on nail surfaces including the nail plate, nail bed, and on other surfaces adjacent to the nail.

TABLE 22

Efficacy of Formulation 1 (Example 1) Against *C. auris* CDC AR Bank #0385

| Contact Time | Test Substance | CFU/mL | Percent Reduction vs. Parallel Time Control | Log$_{10}$ Reduction vs. Parallel Time Control |
|---|---|---|---|---|
| Time Zero | Initial Numbers Control | 5.60E+06 | N/A | |
| 8 hours | Parallel Control | 2.60E+06 | N/A | |
| | Formulation 1 | 1.22E+03 | 99.953% | 3.33 |
| 16 hours | Parallel Control | 7.00E+05 | N/A | |
| | Formulation 1 | 4.50E+02 | 99.936% | 3.19 |
| 24 hours | Parallel Control | 3.75E+06 | N/A | |
| | Formulation 1 | 1.50E+03 | 99.960% | 3.40 |

Example 19. Efficacy of Formulation 1 of Example 1 on *Candida auris* (*C. auris*) CDC AR Bank #0386

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0386 test organism was cultured to produce a test culture. The suspension of test microorganisms was standardized, as needed, by dilution in a buffered saline solution. Test and control substances were dispensed in identical volumes to sterile vessels. 1 gram of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration of plates was performed after ~48 hours incubation. No additional growth or re-colonization was observed after this period.

Figure 11:
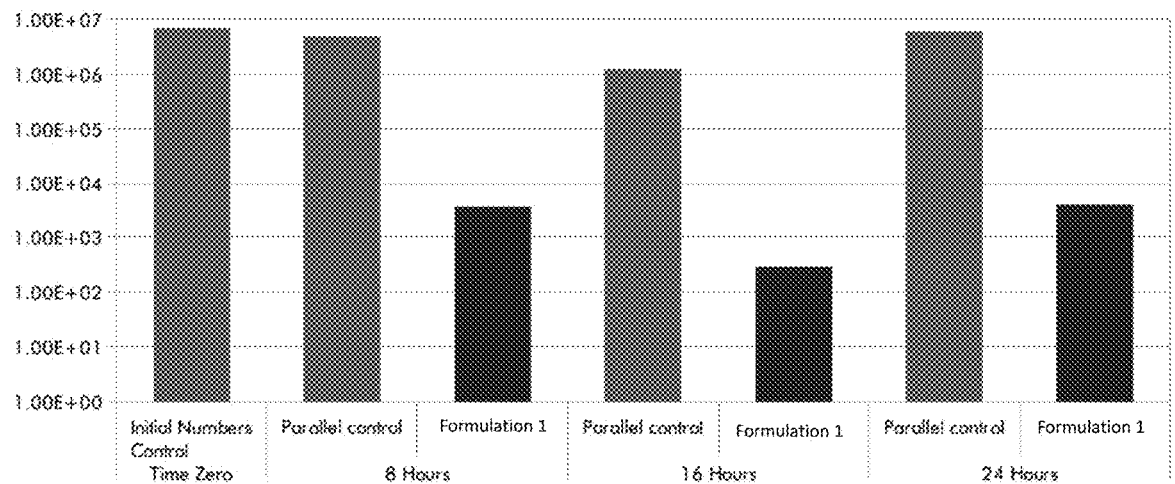
FIG. 11 depicts a graph showing the reduction of *C. auris* CDC AR Bank #0386 test microorganisms according to a ASTM International Method E2315 test following administration of Formulation 1 of Example 1, according to an exemplary embodiment of the present disclosure.

The control substance was phosphate-buffered saline (PBS). The culture growth media and plating media used was potato dextrose agar and the culture dilution media used was PBS. The inoculum concentration was ≥1.0×10$^6$ CFU/mL and the contact time was 8, 16, and 24 hours. 9 mL of D/E broth was used as the neutralizer. The contact temperature was ~25° C.±2° C. (ambient) and the enumeration plate incubation temperature was 28° C.±2° C. The inoculum volume was 0.100 mL and the volume harvested was 1.0 mL The results of the test are shown in Table 23 and FIG. 11. The Percent reduction was determined according to the following formula:

$$\text{Percent Reduction} = \left(\frac{B-A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$Log_{10} Reduction = Log\left(\frac{B}{A}\right),$$

where B equals the number of viable test microorganisms in the control substance immediately after inoculation and A equals the number of viable test microorganisms in the test substance after the contact time. As shown in Table 23 and FIG. 11, Formulation 1 is effective in killing *C. auris* CDC AR Bank #0386 under the conditions of the test. As a result, it is expected that Formulation 1 is effective in the treatment and control of *C. auris* on nail surfaces including the nail plate, nail bed, and on other surfaces adjacent to the nail.

TABLE 23

Efficacy of Formulation 1 (Example 1) Against *C. auris* CDC AR Bank #0386

| Contact Time | Test Substance | CFU/mL | Percent Reduction vs. Parallel Time Control | Log10 Reduction vs. Parallel Time Control |
|---|---|---|---|---|
| Time Zero | Initial Numbers Control | 6.65E+06 | N/A | |
| 8 hours | Parallel Control | 4.70E+06 | N/A | |
| | Formulation 1 | 3.62E+03 | 99.923% | 3.11 |
| 16 hours | Parallel Control | 1.20E+06 | N/A | |
| | Formulation 1 | 2.90E+02 | 99.976% | 3.62 |
| 24 hours | Parallel Control | 5.85E+06 | N/A | |
| | Formulation 1 | 4.00E+03 | 99.932% | 3.17 |

Example 20. Efficacy of Formulation 1 of Example 1 on *Candida auris* (*C. auris*) CDC AR Bank #0389

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0389 test organism was cultured to produce a test culture. The suspension of test microorganisms was standardized, as needed, by dilution in a buffered saline solution. Test and control substances were dispensed in identical volumes to sterile vessels. 1 gram of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration of plates was performed after ~48 hours incubation. No additional growth or re-colonization was observed after this period.

Figure 12:
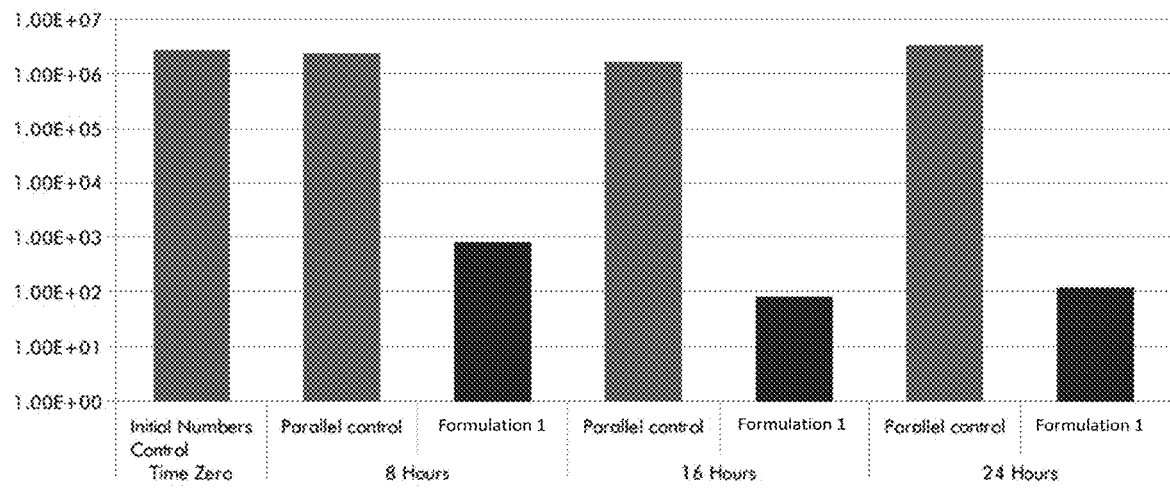
FIG. 12 depicts a graph showing the reduction of *C. auris* CDC AR Bank #0389 test microorganisms according to a ASTM International Method E2315 test following administration of Formulation 1 of Example 1, according to an exemplary embodiment of the present disclosure.

The control substance was phosphate-buffered saline (PBS). The culture growth media and plating media used was potato dextrose agar and the culture dilution media used was PBS. The inoculum concentration was >1.0×10$^6$ CFU/mL and the contact time was 8, 16, and 24 hours. 9 mL of D/E broth was used as the neutralizer. The contact temperature was ~25° C.±2° C. (ambient) and the enumeration plate incubation temperature was 28° C.±2° C. The inoculum volume was 0.100 mL and the volume harvested was 1.0 mL The results of the test are shown in Table 24 and FIG. 12. The Percent reduction was determined according to the following formula:

$$Percent\ Reduction = \left(\frac{B-A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$Log_{10} Reduction = Log\left(\frac{B}{A}\right),$$

where B equals the number of viable test microorganisms in the control substance immediately after inoculation and A equals the number of viable test microorganisms in the test substance after the contact time. As shown in Table 24 and FIG. 12, Formulation 1 is effective in killing *C. auris* CDC AR Bank #0389 under the conditions of the test. As a result, it is expected that Formulation 1 is effective in the treatment and control of *C. auris* on nail surfaces including the nail plate, nail bed, and on other surfaces adjacent to the nail.

TABLE 24

Efficacy of Formulation 1 (Example 1) Against *C. auris* CDC AR Bank #0389

| Contact Time | Test Substance | CFU/mL | Percent Reduction vs. Parallel Time Control | Log$_{10}$ Reduction vs. Parallel Time Control |
|---|---|---|---|---|
| Time Zero | Initial Numbers Control | 2.70E+06 | N/A | |
| 8 hours | Parallel Control | 2.35E+06 | N/A | |
| | Formulation 1 | 8.20E+02 | 99.965% | 3.46 |
| 16 hours | Parallel Control | 1.65E+06 | N/A | |
| | Formulation 1 | 8.00E+01 | 99.995% | 4.31 |
| 24 hours | Parallel Control | 3.20E+06 | N/A | |
| | Formulation 1 | 1.20E+02 | 99.996% | 4.43 |

Example 21. Efficacy of Formulation 1 of Example 1 on *Candida auris* (*C. auris*) CDC AR Bank #0390

A study was conducted on the formulation of Example 1, referred to herein as "Formulation 1" to assess efficacy to treat or control *C. auris*. In particular, ASTM International Standard Test Method E2315 was used as a quantitative test method to assess the antimicrobial activity of Formulation 1 against *C. auris* using a time-kill procedure in an antimicrobial liquid suspension. In the ASTM E2315 test, *C. auris* CDC AR Bank #0390 test organism was cultured to produce a test culture. The suspension of test microorganisms was standardized, as needed, by dilution in a buffered saline solution. Test and control substances were dispensed in identical volumes to sterile vessels. 1 gram of the test substance (Formulation 1) was weighed out and centrifuged to the bottom of conical tubes and mixed by pipette tip with the inoculum. Independently, test and control substances were inoculated with each test microorganism, then mixed and incubated. Control substances were immediately harvested and represent the concentration present at the start of the test, or time zero. At the conclusion of the contact time, a volume of the liquid test solution was harvested and chemically neutralized. Dilutions of the neutralized test solution were assayed using appropriate growth media to determine the surviving microorganisms at the respective contact times. Reductions of microorganisms were calculated by comparing initial microbial concentrations to final microbial concentrations. Enumeration of plates was performed after ~48 hours incubation. No additional growth or re-colonization was observed after this period.

Figure 13:
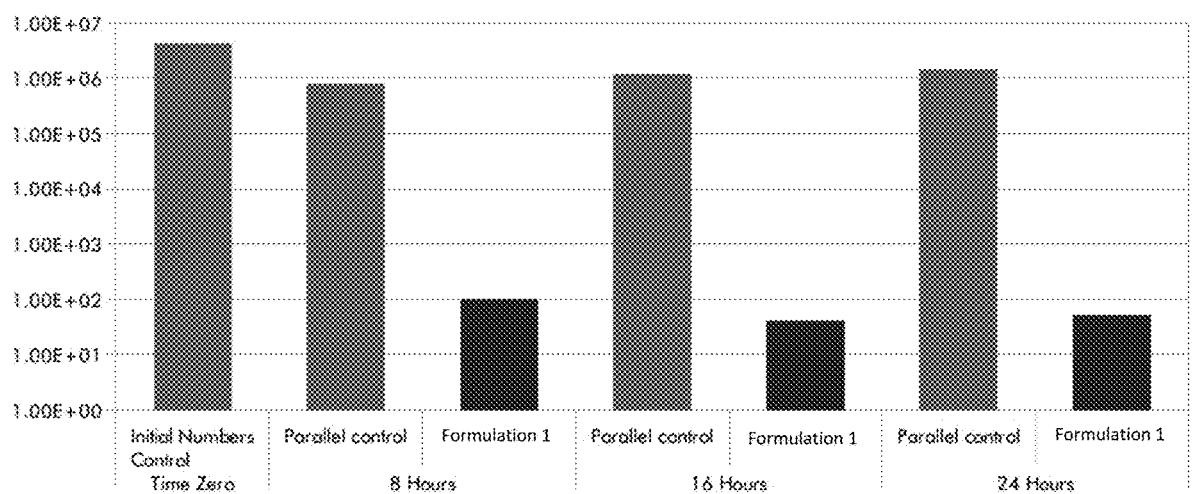
FIG. 13 depicts a graph showing the reduction of *C. auris* CDC AR Bank #0390 test microorganisms according to a ASTM International Method E2315 test following administration of Formulation 1 of Example 1, according to an exemplary embodiment of the present disclosure.

The control substance was phosphate-buffered saline (PBS). The culture growth media and plating media used was potato dextrose agar and the culture dilution media used was PBS. The inoculum concentration was >1.0×10⁶ CFU/mL and the contact time was 8, 16, and 24 hours. 9 mL of D/E broth was used as the neutralizer. The contact temperature was ~25° C.±2° C. (ambient) and the enumeration plate incubation temperature was 28° C.±2° C. The inoculum volume was 0.100 mL and the volume harvested was 1.0 mL The results of the test are shown in Table 25 and FIG. 13. The Percent reduction was determined according to the following formula:

$$\text{Percent Reduction} = \left(\frac{B - A}{B}\right) \times 100,$$

where B equals the number of viable test microorganisms in the control substance immediately after inoculation and A equals the number of viable test microorganisms in the test substance after the contact time. Log 10Reduction was calculated according to the following formula:

$$\text{Log}_{10}\text{Reduction} = \text{Log}\left(\frac{B}{A}\right),$$

where B equals the number of viable test microorganisms in the control substance immediately after inoculation and A equals the number of viable test microorganisms in the test substance after the contact time. As shown in Table 25 and FIG. 13, Formulation 1 is effective in killing *C. auris* CDC AR Bank #0390 under the conditions of the test. As a result, it is expected that Formulation 1 is effective in the treatment and control of *C. auris* on nail surfaces including the nail plate, nail bed, and on other surfaces adjacent to the nail.

TABLE 25

Efficacy of Formulation 1 (Example 1) Against *C. auris* CDC AR Bank #0390

| Contact Time | Test Substance | CFU/mL | Percent Reduction vs. Parallel Time Control | Log₁₀ Reduction vs. Parallel Time Control |
|---|---|---|---|---|
| Time Zero | Initial Numbers Control | 4.05E+06 | N/A | |
| 8 hours | Parallel Control | 8.00E+05 | N/A | |
| | Formulation 1 | 1.00E+02 | 99.988% | 3.90 |
| 16 hours | Parallel Control | 1.15E+06 | N/A | |
| | Formulation 1 | 4.00E+01 | 99.997% | 4.46 |
| 24 hours | Parallel Control | 1.40E+06 | N/A | |
| | Formulation 1 | 5.00E+01 | 99.996% | 4.45 |

Example 22. Topical Administration of Petrolatum-Based PHMB Compositions Improves Clinical Outcomes in Subjects Having Onychomycosis The effect of topical administration of Formulation 1 of Example 1 in the treatment of human subjects having onychomycosis was studied in a clinical setting. During the clinical studies, a group of human subjects having onychomycosis were topically administered the composition of Formulation 1. It was determined that Formulation 1 was 80% effective in curing the onychomycosis after 6 months as compared to a 20% effectiveness of standard of care treatments, such as Lamisil.

Example 23. Topical Administration of Petrolatum-Based PHMB Compositions Improves Clinical Outcomes in Subjects Having Onychomycosis The effect of topical administration of the presently disclosed petrolatum-based PHMB compositions in the treatment of human subjects having onychomycosis will be studied using a randomized, double-blind clinical study. During the clinical study, a group of human subjects will be topically administered one of the presently disclosed PHMB compositions including, but not limited to, Formulation 1. In particular, the petrolatum-based PHMB composition will be applied to the nail of a subject having or otherwise affected by onychomycosis. Subjects receiving treatment using the presently disclosed petrolatum-based PHMB compositions are expected to have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 24. Topical Administration of Petrolatum-Based PHMB Compositions Improves Clinical Outcomes in Subjects Having Onychomycosis Caused by *C. auris*

The effect of topical administration of the presently disclosed PHMB compositions in the treatment of human subjects having onychomycosis caused by *C. auris* will be studied using a randomized, double-blind clinical study. During the clinical study, a group of human subjects will be topically administered one of the presently disclosed PHMB compositions including, but not limited to, Formulation 1. In particular, the petrolatum-based PHMB composition will be applied to a portion of the nail of a subject having or otherwise affected by onychomycosis caused by *C. auris*. Subjects receiving treatment using the presently disclosed petrolatum-based PHMB compositions will have improved standard clinical outcomes. In particular, subjects receiving treatment according to the presently disclosed methods and techniques will exhibit a reduced rate of occurrence of onychomycosis caused by *C. auris* in the portion in the nails or portions thereof receiving treatment as well as reduced clinical signs of onychomycosis caused by *C. auris*.

Example 25. Petrolatum-Based PHMB Compositions Comprising Terbinafine HCl

A petrolatum-based composition in accordance with the present disclosure was prepared by mixing PHMB, Terbinafine HCl and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and from about 0.5% to about 5% by weight terbinafine HCl and greater than 85% petrolatum.

Example 26. Petrolatum-Based PHMB Composition Comprising 1% w/w Terbinafine HCl

A petrolatum-based composition in accordance with the present disclosure was prepared by mixing PHMB, Terbinafine HCl, ethanol, BZK, and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and 1% by weight terbinafine HCl and greater than 85% petrolatum.

Example 27. Petrolatum-Based PHMB Composition Comprising 1% w/w Terbinafine HCl

A petrolatum-based composition in accordance with the present disclosure was prepared by mixing PHMB, ethanol, BZK, and water to form a PHMB solution. The PHMB solution was heated to a temperature from about 1° C. to about 5° C. higher than the temperature of the melted petrolatum and mixed to form a stable petrolatum-based PHMB composition. Terbinafine HCl was added in powdered form to the petrolatum-based PHMB composition and the composition mixed using a mixer to form a petrolatum-based PHMB composition comprising from about 0.05% to about 3% by weight PHMB and 1% by weight terbinafine HCl and greater than 85% petrolatum.

Example 28. Petrolatum-Based PHMB Composition Comprising 1% w/w Terbinafine HCl

A petrolatum-based composition in accordance with the present disclosure was prepared by mixing PHMB, ethanol, BZK, and water to form a PHMB solution. The PHMB solution was heated to a temperature from about 1° C. to about 5° C. higher than the temperature of the melted petrolatum and mixed to form a stable petrolatum-based PHMB composition. The stable petrolatum-based PHMB composition was then heated sufficiently to melt the petrolatum-based PHMB composition to form a melted petrolatum-based PHMB composition. Terbinafine HCl was added in powdered form to the melted petrolatum-based PHMB composition and stirred. The stirred composition was allowed to cool to form a petrolatum-based PHMB composition comprising from about 0.05% to about 3% by weight PHMB and 1% by weight terbinafine HCl and greater than 85% petrolatum.

Example 29. Petrolatum-Based PHMB Compositions Comprising Terbinafine HCl

A petrolatum-based composition in accordance with the present disclosure was prepared by mixing 200 mg of Terbinafine HCl, 100 mL of a 20% PHMB aqueous solution, 162.5 mL of a 80% BZK aqueous solution, 100 mL of ethanol, and 437.5 mL of water to form 1000 mL of a PHMB/Terbinafine HCl solution. Separately, 1900 mL of petrolatum was heated to a temperature sufficient to completely melt the petrolatum and then maintained at that temperature to form melted petrolatum. The 1000 mL PHMB/Terbinafine HCl solution was then heated to a temperature from about 1° C. to about 5° C. higher than the temperature of the melted petrolatum and then mixed with the 19000 mL melted petrolatum and immediately stirred to form a mixture of heated PHMB/Terbinafine HCl solution and melted petrolatum. The heated mixture was then allowed to cool to room temperature to form the petrolatum-based PHMB/Terbinafine HCl composition.

Example 30. Petrolatum-Based PHMB Compositions Comprising Terbinafine HCl

A petrolatum-based composition in accordance with the present disclosure was prepared by mixing 100 mL of a 20% PHMB aqueous solution, 162.5 mL of a 80% BZK aqueous solution, 100 mL of ethanol, and 437.5 mL of water to form 1000 mL of a PHMB solution. Separately, 1900 mL of petrolatum was heated to a temperature sufficient to completely melt the petrolatum and then maintained at that temperature to form melted petrolatum. The 1000 mL PHMB solution was then heated to a temperature from about 1° C. to about 5° C. higher than the temperature of the melted petrolatum and then mixed with the 19000 mL melted petrolatum and immediately stirred to form a mixture of heated PHMB solution and melted petrolatum. The heated mixture was then allowed to cool to room temperature to form the petrolatum-based PHMB composition. The stable petrolatum-based PHMB composition was then heated sufficiently to melt the petrolatum-based PHMB composition to form a melted petrolatum-based PHMB composition. 200 mg of Terbinafine HCl was added in powdered form to the melted petrolatum-based PHMB composition and stirred. The stirred composition was allowed to cool to form a petrolatum-based PHMB composition comprising Terbinafine HCl.

Example 31. Petrolatum-Based PHMB Compositions Comprising Terbinafine HCl

A petrolatum-based composition in accordance with the present disclosure was prepared by mixing 100 mL of a 20% PHMB aqueous solution, 162.5 mL of a 80% BZK aqueous solution, 100 mL of ethanol, and 437.5 mL of water to form 1000 mL of a PHMB solution. Separately, 1900 mL of petrolatum was heated to a temperature sufficient to completely melt the petrolatum and then maintained at that temperature to form melted petrolatum. The 1000 mL PHMB solution was then heated to a temperature from about 1° C. to about 5° C. higher than the temperature of the melted petrolatum and then mixed with the 19000 mL melted petrolatum and immediately stirred to form a mixture of heated PHMB solution and melted petrolatum. The heated mixture was then allowed to cool to room temperature to form the petrolatum-based PHMB composition. 200 mg of Terbinafine HCl powder was added to the petrolatum-based PHMB composition and mixed using a mixer to form a petrolatum-based PHMB composition comprising Terbinafine HCl.

Example 32. Topical Administration of Petrolatum-Based PHMB Compositions Comprising Terbinafine HCl Improves Clinical Outcomes in Subjects Having Onychomycosis The effect of topical administration of any one of the petrolatum-based PHMB compositions comprising terbinafine HCl disclosed in Examples 25-31 in the treatment of human subjects having onychomycosis will be studied using a randomized, double-blind clinical study. During the clinical study, a group of human subjects will be topically administered one of the compositions according to Examples 25-31. In particular, the petrolatum-based PHMB composition comprising terbinafine HCl will be applied to the nail of a subject having or otherwise affected by onychomycosis. Subjects receiving such treatment will have improved standard clinical outcomes. In particular, subjects receiving treatment according to the presently disclosed methods and techniques are will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 33. Petrolatum-Based PHMB Compositions Comprising Ciclopirox

A petrolatum-based composition in accordance with the present disclosure was prepared by mixing PHMB, ciclopirox and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and from about 0.5% to about 5% by weight ciclopirox and greater than 85% petrolatum.

Example 34. Petrolatum-Based PHMB Composition Comprising 1% w/w Ciclopirox

A petrolatum-based composition in accordance with the present disclosure was prepared by mixing PHMB, Ciclopirox, ethanol, BZK, and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and 1% by weight Ciclopirox and greater than 85% petrolatum.

Example 35. Petrolatum-Based PHMB Compositions Comprising Ciclopirox

A petrolatum-based composition in accordance with the present disclosure was prepared by mixing 200 mg of Ciclopirox, 100 mL of a 20% PHMB aqueous solution, 162.5 mL of a 80% BZK aqueous solution, 100 mL of ethanol, and 437.5 mL of water to form 1000 mL of a PHMB/Ciclopirox solution. Separately, 1900 mL of petrolatum was heated to a temperature sufficient to completely melt the petrolatum and then maintained at that temperature to form melted petrolatum. The 1000 mL PHMB/Ciclopirox solution was then heated to a temperature from about 1° C. to about 5° C. higher than the temperature of the melted petrolatum and then mixed with the 19000 mL melted petrolatum and immediately stirred to form a mixture of heated PHMB/Ciclopirox and melted petrolatum. The heated mixture was then allowed to cool to room temperature to form the petrolatum-based PHMB/Ciclopirox composition.

Example 36. Topical Administration of Petrolatum-Based PHMB Compositions Comprising Ciclopirox Improves Clinical Outcomes in Subjects Having Onychomycosis The effect of topical administration of any one of the petrolatum-based PHMB compositions comprising ciclopirox described in Examples 33-35 in the treatment of human subjects having onychomycosis will be studied using a randomized, double-blind clinical study. During the clinical study, a group of human subjects will be topically administered one of the compositions described in Examples 33-35. In particular, the petrolatum-based PHMB composition comprising ciclopirox will be applied to the nail of a subject having or otherwise affected by onychomycosis. Subjects receiving such treatment will have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes are expected for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 37. Petrolatum-Based PHMB Compositions Comprising Ciclopirox Olamine A petrolatum-based composition in accordance with the present disclosure was prepared by mixing PHMB, ciclopirox olamine and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and from about 0.5% to about 5% by weight ciclopirox olamine and greater than 85% petrolatum.

Example 38. Petrolatum-Based PHMB Composition Comprising 1% w/w Ciclopirox Olamine A petrolatum-based composition in accordance with the present disclosure was prepared by mixing PHMB, Ciclopirox Olamine, ethanol, BZK, and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and 1% by weight Ciclopirox Olamine and greater than 85% petrolatum.

Example 39. Petrolatum-Based PHMB Compositions Comprising Ciclopirox Olamine

A petrolatum-based composition in accordance with the present disclosure was prepared by mixing 200 mg of Ciclopirox Olamine, 100 mL of a 20% PHMB aqueous solution, 162.5 mL of a 80% BZK aqueous solution, 100 mL of ethanol, and 437.5 mL of water to form 1000 mL of a PHMB/Ciclopirox Olamine solution. Separately, 1900 mL of petrolatum was heated to a temperature sufficient to completely melt the petrolatum and then maintained at that temperature to form melted petrolatum. The 1000 mL PHMB/Ciclopirox Olamine solution was then heated to a temperature from about 1° C. to about 5° C. higher than the temperature of the melted petrolatum and then mixed with the 19000 mL melted petrolatum and immediately stirred to form a mixture of heated PHMB/Ciclopirox Olamine and melted petrolatum. The heated mixture was then allowed to cool to room temperature to form the petrolatum-based PHMB/Ciclopirox Olamine composition.

Example 40. Topical Administration of Petrolatum-Based PHMB Compositions Comprising Ciclopirox Olamine Improves Clinical Outcomes in Subjects Having Onychomycosis The effect of topical administration of any one of the petrolatum-based PHMB compositions comprising ciclopirox olamine described in Examples 37-39 in the treatment of human subjects having onychomycosis will be studied using a randomized, double-blind clinical study. During the clinical study, a group of human subjects will be topically administered one of the compositions described in Examples 37-39. In particular, the petrolatum-based PHMB composition comprising ciclopirox olamine will be applied to the nail of a subject having or otherwise affected by onychomycosis. Subjects receiving such treatment will have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes are expected for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 41. Petrolatum-Based PHMB Compositions Comprising Fluconazole

A petrolatum-based composition in accordance with the present disclosure was prepared by mixing PHMB, fluconazole and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and from about 0.5% to about 5% by weight fluconazole and greater than 85% petrolatum.

Example 42. Topical Administration of Petrolatum-Based PHMB Compositions Comprising Fluconazole Improves Clinical Outcomes in Subjects Having Onychomycosis The effect of topical administration of the petrolatum-based PHMB composition comprising fluconazole of Example 41 in the treatment of human subjects having onychomycosis will be studied using a randomized, double-blind clinical study. During the clinical study, a group of human subjects will be topically administered the composition of Example 41. In particular, the petrolatum-based PHMB composition comprising fluconazole will be applied to the nail of a subject having or otherwise affected by onychomycosis. Subjects receiving such treatment will have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes are expected for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 43. Petrolatum-Based PHMB Compositions Comprising Itraconazole, Ketoconazole, Amorolfine, Efinaconazole, Clotrimazole, or Miconazole (Miconazole Nitrate)

A petrolatum-based composition in accordance with the present disclosure was prepared by mixing PHMB and itraconazole, ketoconazole, amorolfine, efinaconazole, clotrimazole, or miconazole (miconazole nitrate), and water to form a PHMB solution. The PHMB solution was heated to a temperature from about 1° C. to about 5° C. higher than the temperature of the melted petrolatum and mixed to form a stable petrolatum-based PHMB composition comprising from about 0.05% to about 3% by weight PHMB and from about 0.5% to about 5% by weight itraconazole, ketoconazole, amorolfine, efinaconazole, clotrimazole, or miconazole (miconazole nitrate) and greater than 85% petrolatum.

Example 44. Topical Administration of Petrolatum-Based PHMB Compositions Comprising Itraconazole, Ketoconazole, Amorolfine, Efinaconazole, Clotrimazole, or Miconazole (Miconazole Nitrate) Improves Clinical Outcomes in Subjects Having Onychomycosis The effect of topical administration of the petrolatum-based PHMB composition comprising itraconazole, ketoconazole, amorolfine, efinaconazole, clotrimazole, or miconazole (miconazole nitrate) of Example 43 in the treatment of human subjects having onychomycosis will be studied using a randomized, double-blind clinical study. During the clinical study, a group of human subjects will be topically administered the composition of Example 43. In particular, the petrolatum-based PHMB composition comprising itraconazole, ketoconazole, amorolfine, efinaconazole, clotrimazole, or miconazole (miconazole nitrate) will be applied to the nail of a subject having or otherwise affected by onychomycosis. Subjects receiving such treatment will have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes are expected for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 45. Petrolatum-Based PAPB Composition

Example 1 was repeated but with substitution of the chemically similar polyaminopropyl biguanide (PAPB) for PHMB to form a petrolatum-based PAPB composition. Specifically, 2540.3 pounds of white petrolatum was added to a tank that has been cleaned and sterilized in accordance with SOP protocol. In the tank was used to heat the petrolatum to 110° C. to 113° F. to melt the petrolatum. In a separate clean and sanitized container 133.70 pounds of water and the desired amount of BZK and PAPB were added and heated to 122° F. When both phases were at temperature, the solution phase was slowly added to the petrolatum with mixing. The heat was decreased slowly to 96 to 104° F. The product was tested for quality control and transferred to polypropylene drums. The resulting composition was shiny and white to slightly yellow in appearance. Specific gravity at 25° C. matches specification when it is from 0.830-0.910. Viscosity at @ 25° C. TF @ 10 rpm matches specification when it is from about 225,000-300,000 cps. The final formulation contained the following ingredients by weight percent: 95% petrolatum, 0.13% BZK, 0.2% PAPB, and 4.67% water.

Example 46. Petrolatum-Based PAPB Composition Comprising 1% w/w Terbinafine HCl

A petrolatum-based composition in accordance with the present disclosure was prepared by mixing PAPB, ethanol, BZK, and water to form a PAPB solution. The PAPB solution was heated to a temperature from about 1° C. to about 5° C. higher than the temperature of the melted petrolatum and mixed to form a stable petrolatum-based PAPB composition. The stable petrolatum-based PAPB composition was then heated sufficiently to melt the petrolatum-based PAPB composition to form a melted petrolatum-based PAPB composition. Terbinafine HCl was added in powdered form to the melted petrolatum-based PAPB composition and stirred. The stirred composition was allowed to cool to form a petrolatum-based PAPB composition comprising from about 0.05% to about 3% by weight PAPB and 1% by weight terbinafine HCl and greater than 85% petrolatum.

Example 47. Topical Administration of Petrolatum-Based PAPB Compositions Improves Clinical Outcomes in Subjects Having Onychomycosis The effect of topical administration of the presently disclosed petrolatum-based PAPB compositions in the treatment of human subjects having onychomycosis will be studied using a randomized, double-blind clinical study. During the clinical study, a group of human subjects will be topically administered one of the presently disclosed PAPB compositions including, but not limited to, the composition of Example 45 or 46. In particular, the petrolatum-based PAPB composition will be applied to the nail of a subject having or otherwise affected by onychomycosis. Subjects receiving treatment using the presently disclosed petrolatum-based PAPB compositions are expected to have improved standard clinical outcomes. In particular, subjects receiving treatment according to the presently disclosed methods and techniques will exhibit a reduced rate of occurrence of onychomycosis in the nails or portions thereof receiving treatment as well as reduced clinical signs of onychomycosis. Similar improved standard clinical outcomes will be obtained for subjects having onychomycosis caused by *T. rubrum, Candida*, as well as for the distal subungual onychomycosis, white superficial onychomycosis (WSO), proximal subungual onychomycosis, and Candidal onychomycosis sub-types of onychomycosis.

Example 48. Topical Administration of Petrolatum-Based PAPB Compositions Improves Clinical Outcomes in Subjects Having Onychomycosis Caused by *C. auris*

The effect of topical administration of the presently disclosed PAPB compositions in the treatment of human subjects having onychomycosis caused by *C. auris* will be studied using a randomized, double-blind clinical study. During the clinical study, a group of human subjects will be topically administered one of the presently disclosed PAPB compositions including, but not limited to, the compositions of Example 45 or 46. In particular, the petrolatum-based PAPB composition will be applied to a portion of the nail of a subject having or otherwise affected by onychomycosis caused by *C. auris*. Subjects receiving treatment using the presently disclosed petrolatum-based PAPB compositions will have improved standard clinical outcomes. In particular, subjects receiving treatment according to the presently disclosed methods and techniques will exhibit a reduced rate of occurrence of onychomycosis caused by *C. auris* in the portion in the nails or portions thereof receiving treatment as well as reduced clinical signs of onychomycosis caused by *C. auris*.

Statements of the Disclosure:

Numerous examples are provided herein to enhance understanding of the present disclosure. A specific set of statements are provided as follows.

Statement 1: A method of treating onychomycosis in a subject, the method comprising applying a petrolatum-based polyhexamethylene biguanide (PHMB) composition to the nail of a subject in need of treatment.

Statement 2: A method according to Statement 1, wherein the onychomycosis is caused by *Trichophyton rubrum* (*T. rubrum*).

Statement 3: A method according to Statement 1, wherein the onychomycosis is caused by *Candida*.

Statement 4: A method according to Statement 1, wherein the onychomycosis is distal subungual onychomycosis.

Statement 5: A method according to Statement 1, wherein the onychomycosis is white superficial onychomycosis (WSO).

Statement 6: A method according to Statement 1, wherein the onychomycosis is proximal subungual onychomycosis.

Statement 7: A method according to Statement 1, wherein the onychomycosis is Candidal onychomycosis.

Statement 8: A method according to Statement 7, wherein the Candidal onychomycosis is caused by *Candida auris* (*C. auris*).

Statement 9: A method according to Statement 8, wherein the *C. auris* is multi-drug resistant *C. auris*.

Statement 10: A method according to any one of the preceding Statements 1-9, wherein the petrolatum-based PHMB composition comprises from about 0.005% to about 5% by weight PHMB.

Statement 11: A method according to any one of the preceding Statements 1-9, wherein the petrolatum-based PHMB composition comprises from about 0.01% to about 5% by weight PHMB.

Statement 12: A method according to any one of the preceding Statements 1-9, wherein the petrolatum-based PHMB composition comprises from about 0.05% to about 5% by weight PHMB.

Statement 13: A method according to any one of the preceding Statements 1-9, wherein the petrolatum-based PHMB composition comprises from about 0.05% to about 3% by weight PHMB.

Statement 14: A method according to any one of the preceding Statements 1-9, wherein the petrolatum-based PHMB composition comprises from about 0.1% to about 1% by weight PHMB.

Statement 15: A method according to any one of the preceding Statements 1-9, wherein the petrolatum-based PHMB composition comprises from about 0.2% to about 0.6% by weight PHMB.

Statement 16: A method according to any one of the preceding Statements 1-9, wherein the petrolatum-based PHMB composition comprises from about 0.3% to about 0.5% by weight PHMB.

Statement 17: A method according to any one of the preceding Statements 1-9, wherein the petrolatum-based PHMB composition comprises from about 0.1% to about 3.5% by weight PHMB.

Statement 18: A method according to any one of the preceding Statements 1-9, wherein the petrolatum-based PHMB composition comprises from about 0.05% to about 2.5% by weight PHMB.

Statement 19: A method according to any one of the preceding Statements 1-9, wherein the petrolatum-based PHMB composition comprises from about 0.5% to about 3% by weight PHMB.

Statement 20: A method according to any one of the preceding Statements 1-9, wherein the petrolatum-based PHMB composition comprises from about 0.5% to about 2.5% by weight PHMB.

Statement 21: A method according to any one of the preceding Statements 1-9, wherein the petrolatum-based PHMB composition comprises from about 1.5% to about 2.5% by weight PHMB.

Statement 22: A method according to any one of the preceding Statements 1-21, wherein the petrolatum-based PHMB composition comprises greater than about 80% by weight petrolatum.

Statement 23: A method according to any one of the preceding Statements 1-21, wherein the petrolatum-based PHMB composition comprises greater than about 90% by weight petrolatum.

Statement 24: A method according to any one of the preceding Statements 1-21, wherein the petrolatum-based PHMB composition comprises greater than about 95% by weight petrolatum.

Statement 25: A method according to any one of the preceding Statements 1-24, wherein the petrolatum-based PHMB composition contains no emulsifier.

Statement 26: A method according to any one of the preceding Statements 1-24, wherein the petrolatum-based PHMB composition excludes an added emulsifier.

Statement 27: A method according to any one of the preceding Statements 1-26, wherein the petrolatum-based PHMB composition further includes a cationic biocide selected from the group consisting of benzalkonium chloride, cetrimide, chlorhexidine, and any combination thereof.

Statement 28: A method according to Statement 27, wherein the petrolatum-based PHMB composition comprises from about 0.001% to about 0.15% by weight benzalkonium chloride (BZK).

Statement 29: A method according to Statement 27, wherein the petrolatum-based PHMB composition comprises from about 0.001% to about 0.01% by weight or from about 0.005% to about 0.007% by weight benzalkonium chloride (BZK).

Statement 30: A method according to any one of the preceding Statements 1-29, wherein the petrolatum-based PHMB composition is prepared by a process comprising: a) dissolving the PHMB in a polar solvent to give a PHMB solution; b) heating the petrolatum to a temperature sufficient to cause the petrolatum to melt to give a melted petrolatum and heating the PHMB solution to a temperature higher than the temperature of the melted petrolatum to give a heated PHMB solution; c) mixing the melted petrolatum and the heated PHMB solution to give a melted mixture; and d) cooling the melted mixture to give the petrolatum-based PHMB composition.

Statement 31: A method according to Statement 30, wherein the heated PHMB solution has a temperature that is about 1° C. to about 5° C. higher than the temperature of the melted petrolatum.

Statement 32: A method according to Statement 30 or Statement 31, wherein the PHMB is dissolved in a polar solvent to form a PHMB solution, the PHMB solution dispersed in the petrolatum to form a stable suspension.

Statement 33: A method according to any one of the preceding Statements 1-32, wherein the petrolatum-based PHMB composition further comprises at least one additional anti-fungal agent selected from the group consisting of terbinafine HCl, ciclopirox, ciclopirox olamine, fluconazole, itraconazole, ketoconazole, amorolfine, efinaconazole, clotrimazole, miconazole (miconazole nitrate) and any combination thereof.

Statement 34: A method according to Statement 33, wherein the PHMB and the at least one additional anti-fungal agent are dissolved in a polar solvent to form a PHMB solution, the PHMB solution dispersed in the petrolatum to form a stable suspension.

Statement 35: A method according to claim any one of the preceding Statements 30-34, wherein the polar solvent is selected from the group consisting of water, ethanol, and any combination thereof.

Statement 36: A method according to any one of the preceding Statements 1-35, wherein the petrolatum-based PHMB composition further comprises from about 0.01% to about 5%, or from about 0.001% to about 5%, or from about 0.05% to about 5% by weight terbinafine HCl.

Statement 37: A method according to any one of the preceding Statements 1-35, wherein the petrolatum-based PHMB composition further comprises from about 0.01% to about 5%, or from about 0.001% to about 5%, or from about 0.05% to about 5% by weight ciclopirox.

Statement 38: A method according to any one of the preceding Statements 1-35, wherein the petrolatum-based PHMB composition further comprises from about 0.01% to about 5%, or from about 0.001% to about 5%, or from about 0.05% to about 5% by weight ciclopirox olamine.

Statement 39: A method according to any one of the preceding Statements 1-35, wherein the petrolatum-based PHMB composition further comprises from about 0.01% to about 5%, or from about 0.001% to about 5%, or from about 0.05% to about 5% by weight fluconazole.

Statement 40: A method according to any one of the preceding Statements 1-35, wherein the petrolatum-based PHMB composition further comprises from about 0.01% to about 5%, or from about 0.001% to about 5%, or from about 0.05% to about 5% by weight itraconazole.

Statement 41: A method according to any one of the preceding Statements 1-35, wherein the petrolatum-based PHMB composition further comprises from about 0.01% to about 5%, or from about 0.001% to about 5%, or from about 0.05% to about 5% by weight ketoconazole.

Statement 42: A method according to any one of the preceding Statements 1-35, wherein the petrolatum-based PHMB composition further comprises from about 0.01% to about 5%, or from about 0.001% to about 5%, or from about 0.05% to about 5% by weight amorolfine.

Statement 43: A method according to any one of the preceding Statements 1-35, wherein the petrolatum-based PHMB composition further comprises from about 0.01% to about 5%, or from about 0.001% to about 5%, or from about 0.05% to about 5% by weight efinaconazole.

Statement 44: A petrolatum-based PHMB composition for the treatment of onychomycosis, the composition comprising a pharmaceutically effective amount of polyhexamethylene biguanide (PHMB) in a petrolatum carrier.

Statement 45: A composition according to Statement 44, wherein the onychomycosis is caused by *Trichophyton rubrum* (*T. rubrum*).

Statement 46: A composition according to Statement 44, wherein the onychomycosis is caused by *Candida*.

Statement 47: A composition according to Statement 44, wherein the onychomycosis is distal subungual onychomycosis.

Statement 48: A composition according to Statement 44, wherein the onychomycosis is white superficial onychomycosis (WSO).

Statement 49: A composition according to Statement 44, wherein the onychomycosis is proximal subungual onychomycosis.

Statement 50: A composition according to Statement 44, wherein the onychomycosis is Candidal onychomycosis.

Statement 51: A composition according to Statement 46, wherein the Candidal onychomycosis is caused by *Candida auris* (*C. auris*).

Statement 52: A composition according to Statement 51, wherein the *C. auris* is multi-drug resistant *C. auris*.

Statement 53: A composition according to any one of the preceding Statements 44-52, wherein the petrolatum-based PHMB composition comprises from about 0.005% to about 5% by weight PHMB.

Statement 54: A composition according to any one of the preceding Statements 44-52, wherein the petrolatum-based PHMB composition comprises from about 0.01% to about 5% by weight PHMB.

Statement 55: A composition according to any one of the preceding Statements 44-52, wherein the petrolatum-based PHMB composition comprises from about 0.05% to about 5% by weight PHMB.

Statement 56: A composition according to any one of the preceding Statements 44-52, wherein the petrolatum-based PHMB composition comprises from about 0.05% to about 3% by weight PHMB.

Statement 57: A composition according to any one of the preceding Statements 44-52, wherein the petrolatum-based PHMB composition comprises from about 0.1% to about 1% by weight PHMB.

Statement 58: A composition according to any one of the preceding Statements 44-52, wherein the petrolatum-based PHMB composition comprises from about 0.2% to about 0.6% by weight PHMB.

Statement 59: A composition according to any one of the preceding Statements 44-52, wherein the petrolatum-based PHMB composition comprises from about 0.3% to about 0.5% by weight PHMB.

Statement 60: A composition according to any one of the preceding Statements 44-52, wherein the petrolatum-based PHMB composition comprises from about 0.1% to about 3.5% by weight PHMB.

Statement 61: A composition according to any one of the preceding Statements 44-52, wherein the petrolatum-based PHMB composition comprises from about 0.05% to about 2.5% by weight PHMB.

Statement 62: A composition according to any one of the preceding Statements 44-52, wherein the petrolatum-based PHMB composition comprises from about 0.5% to about 3% by weight PHMB.

Statement 63: A composition according to any one of the preceding Statements 44-52, wherein the petrolatum-based PHMB composition comprises from about 0.5% to about 2.5% by weight PHMB.

Statement 64: A composition according to any one of the preceding Statements 44-52, wherein the petrolatum-based PHMB composition comprises from about 1.5% to about 2.5% by weight PHMB.

Statement 65: A composition according to any one of the preceding Statements 44-64, wherein the petrolatum-based PHMB composition comprises greater than about 80% by weight petrolatum.

Statement 66: A composition according to any one of the preceding Statements 44-64, wherein the petrolatum-based PHMB composition comprises greater than about 90% by weight petrolatum.

Statement 67: A composition according to any one of the preceding Statements 44-64, wherein the petrolatum-based PHMB composition comprises greater than about 95% by weight petrolatum.

Statement 68: A composition according to any one of the preceding Statements 44-67, wherein the petrolatum-based PHMB composition contains no emulsifier.

Statement 69: A composition according to any one of the preceding Statements 44-67, wherein the petrolatum-based PHMB composition excludes an added emulsifier.

Statement 70: A composition according to any one of the preceding Statements 44-69, wherein the petrolatum-based PHMB composition further includes a cationic biocide selected from the group consisting of benzalkonium chloride, cetrimide, chlorhexidine, and any combination thereof.

Statement 71: A composition according to Statement 70, wherein the petrolatum-based PHMB composition comprises from about 0.001% to about 0.15% by weight benzalkonium chloride (BZK).

Statement 72: A composition according to Statement 70, wherein the petrolatum-based PHMB composition comprises from about 0.001% to about 0.01% by weight or from about 0.005% to about 0.007% by weight benzalkonium chloride (BZK).

Statement 73: A composition according to any one of the preceding Statements 44-72, wherein the petrolatum-based PHMB composition is prepared by a process comprising: a) dissolving the PHMB in a polar solvent to give a PHMB solution; b) heating the petrolatum to a temperature sufficient to cause the petrolatum to melt to give a melted petrolatum and heating the PHMB solution to a temperature higher than the temperature of the melted petrolatum to give a heated PHMB solution; c) mixing the melted petrolatum and the heated PHMB solution to give a melted mixture; and d) cooling the melted mixture to give the petrolatum-based PHMB composition.

Statement 74: A composition according to Statement 73, wherein the heated PHMB solution has a temperature that is about 1° C. to about 5° C. higher than the temperature of the melted petrolatum.

Statement 75: A composition according to Statement 73 or Statement 74, wherein the PHMB is dissolved in a polar solvent to form a PHMB solution, the PHMB solution dispersed in the petrolatum to form a stable suspension.

Statement 76: A composition according to any one of the preceding Statements 44-75, wherein the petrolatum-based PHMB composition further comprises at least one additional anti-fungal agent selected from the group consisting of terbinafine HCl, ciclopirox, ciclopirox olamine, fluconazole, itraconazole, ketoconazole, amorolfine, efinaconazole, clotrimazole, miconazole (miconazole nitrate), and any combination thereof.

Statement 77: A composition according to Statement 76, wherein the PHMB and the at least one additional anti-fungal agent are dissolved in a polar solvent to form a PHMB solution, the PHMB solution dispersed in the petrolatum to form a stable suspension.

Statement 78: A composition according to any one of the preceding Statements 73-77, wherein the polar solvent is selected from the group consisting of water, ethanol, and any combination thereof.

Statement 79: A composition according to any one of the preceding Statements 44-78, wherein the petrolatum-based PHMB composition further comprises from about 0.01% to about 5%, or from about 0.001% to about 5%, or from about 0.05% to about 5% by weight terbinafine HCl.

Statement 80: A composition according to any one of the preceding Statements 44-78, wherein the petrolatum-based PHMB composition further comprises from about 0.01% to about 5%, or from about 0.001% to about 5%, or from about 0.05% to about 5% by weight ciclopirox.

Statement 81: A composition according to any one of the preceding Statements 44-78, wherein the petrolatum-based PHMB composition further comprises from about 0.01% to about 5%, or from about 0.001% to about 5%, or from about 0.05% to about 5% by weight ciclopirox olamine.

Statement 82: A composition according to any one of the preceding Statements 44-78, wherein the petrolatum-based PHMB composition further comprises from about 0.01% to about 5%, or from about 0.001% to about 5%, or from about 0.05% to about 5% by weight fluconazole.

Statement 83: A composition according to any one of the preceding Statements 44-78, wherein the petrolatum-based PHMB composition further comprises from about 0.01% to about 5%, or from about 0.001% to about 5%, or from about 0.05% to about 5% by weight itraconazole.

Statement 84: A composition according to any one of the preceding Statements 44-78, wherein the petrolatum-based PHMB composition further comprises from about 0.01% to about 5%, or from about 0.001% to about 5%, or from about 0.05% to about 5% by weight ketoconazole.

Statement 85: A composition according to any one of the preceding Statements 44-78, wherein the petrolatum-based PHMB composition further comprises from about 0.01% to about 5%, or from about 0.001% to about 5%, or from about 0.05% to about 5% by weight amorolfine.

Statement 86: A composition according to any one of the preceding Statements 44-78, wherein the petrolatum-based PHMB composition further comprises from about 0.01% to about 5%, or from about 0.001% to about 5%, or from about 0.05% to about 5% by weight efinaconazole.

Statement 87: A composition according to any one of the preceding Statements 44-78, wherein the petrolatum-based PHMB composition further comprises from about 0.01% to about 5%, or from about 0.001% to about 5%, or from about 0.05% to about 5% by weight clotrimazole.

Statement 88: A composition according to any one of the preceding Statements 44-78, wherein the petrolatum-based PHMB composition further comprises from about 0.01% to about 5%, or from about 0.001% to about 5%, or from about 0.05% to about 5% by weight miconazole (miconazole nitrate).

Statement 89: A method according to any one of the preceding Statements 1-35, wherein the petrolatum-based PHMB composition further comprises from about 0.01% to about 5%, or from about 0.001% to about 5%, or from about 0.05% to about 5% by weight clotrimazole.

Statement 90: A method according to any one of the preceding Statements 1-35, wherein the petrolatum-based PHMB composition further comprises from about 0.01% to about 5%, or from about 0.001% to about 5%, or from about 0.05% to about 5% by weight miconazole (miconazole nitrate).

Statement 91: A method of treating onychomycosis in a subject, the method comprising applying a petrolatum-based composition to the nail of a subject in need of treatment, wherein the petrolatum-based composition comprises one or more cationic biocides, the one or more cationic biocides selected from the group consisting of polyhexamethylene biguanide (PHMB), polyaminopropyl biguanide (PAPB), chlorhexidine (CHG), and any combination thereof.

Statement 92: A method according to Statement 91, wherein the onychomycosis is caused by *Trichophyton rubrum* (*T. rubrum*).

Statement 93: A method according to Statement 91, wherein the onychomycosis is caused by *Candida*.

Statement 94: A method according to Statement 91, wherein the onychomycosis is distal subungual onychomycosis.

Statement 95: A method according to Statement 91, wherein the onychomycosis is white superficial onychomycosis (WSO).

Statement 96: A method according to Statement 91, wherein the onychomycosis is proximal subungual onychomycosis.

Statement 97: A method according to Statement 91, wherein the onychomycosis is Candidal onychomycosis.

Statement 98: A method according to Statement 97, wherein the Candidal onychomycosis is caused by *Candida auris* (*C. auris*).

Statement 99: A method according to Statement 98, wherein the *C. auris* is multi-drug resistant *C. auris*.

Statement 100: A method according to any one of the preceding Statements 91-99, wherein the petrolatum-based composition comprises from about 0.005% to about 5% by weight cationic biocide.

Statement 101: A method according to any one of the preceding Statements 91-99, wherein the petrolatum-based composition comprises from about 0.01% to about 5% by weight cationic biocide.

Statement 102: A method according to any one of the preceding Statements 91-99, wherein the petrolatum-based composition comprises from about 0.05% to about 5% by weight PHMB.

Statement 103: A method according to any one of the preceding Statements 91-99, wherein the petrolatum-based PHMB composition comprises from about 0.05% to about 3% by weight PHMB.

Statement 104: A method according to any one of the preceding Statements 91-99, wherein the petrolatum-based composition comprises from about 0.1% to about 1% by weight cationic biocide.

Statement 105: A method according to any one of the preceding Statements 91-99, wherein the petrolatum-based composition comprises from about 0.2% to about 0.6% by weight cationic biocide.

Statement 106: A method according to any one of the preceding Statements 91-99, wherein the petrolatum-based composition comprises from about 0.3% to about 0.5% by weight cationic biocide.

Statement 107: A method according to any one of the preceding Statements 91-99, wherein the petrolatum-based composition comprises from about 0.1% to about 3.5% by weight cationic biocide.

Statement 108: A method according to any one of the preceding Statements 91-99, wherein the petrolatum-based composition comprises from about 0.05% to about 2.5% by weight cationic biocide.

Statement 109: A method according to any one of the preceding Statements 91-99, wherein the petrolatum-based composition comprises from about 0.5% to about 3% by weight cationic biocide.

Statement 110: A method according to any one of the preceding Statements 91-99, wherein the petrolatum-based composition comprises from about 0.5% to about 2.5% by weight cationic biocide.

Statement 111: A method according to any one of the preceding Statements 91-99, wherein the petrolatum-based composition comprises from about 1.5% to about 2.5% by weight cationic biocide.

Statement 112: A method according to any one of the preceding Statements 91-111, wherein the petrolatum-based composition comprises greater than about 80% by weight petrolatum.

Statement 113: A method according to any one of the preceding Statements 91-111, wherein the petrolatum-based composition comprises greater than about 90% by weight petrolatum.

Statement 114: A method according to any one of the preceding Statements 91-112, wherein the petrolatum-based composition comprises greater than about 95% by weight petrolatum.

Statement 115: A method according to any one of the preceding Statements 91-114, wherein the petrolatum-based composition contains no emulsifier.

Statement 116: A method according to any one of the preceding Statements 91-114, wherein the petrolatum-based composition excludes an added emulsifier.

Statement 117: A method according to any one of the preceding Statements 91-116, wherein the petrolatum-based composition further includes a cationic biocide selected from the group consisting of benzalkonium chloride, cetrimide, and any combination thereof.

Statement 118: A method according to Statement 117, wherein the petrolatum-based composition comprises from about 0.001% to about 0.15% by weight benzalkonium chloride (BZK).

Statement 119: A method according to Statement 117, wherein the petrolatum-based composition comprises from about 0.001% to about 0.01% by weight or from about 0.005% to about 0.007% by weight benzalkonium chloride (BZK).

Statement 120: A method according to any one of the preceding Statements 91-119, wherein the petrolatum-based composition is prepared by a process comprising: a) dissolving the cationic biocide in a polar solvent to give a cationic biocide solution; b) heating the petrolatum to a temperature sufficient to cause the petrolatum to melt to give a melted petrolatum and heating the cationic biocide solution to a temperature higher than the temperature of the melted petrolatum to give a heated cationic biocide solution; c) mixing the melted petrolatum and the heated cationic biocide solution to give a melted mixture; and d) cooling the melted mixture to give the petrolatum-based cationic biocide composition.

Statement 121: A method according to Statement 120, wherein the heated cationic biocide solution has a temperature that is about 1° C. to about 5° C. higher than the temperature of the melted petrolatum.

Statement 122: A method according to Statement 120 or Statement 121, wherein the cationic biocide is dissolved in a polar solvent to form a cationic biocide solution, the cationic biocide solution dispersed in the petrolatum to form a stable suspension.

Statement 123: A method according to any one of the preceding Statements 91-122, wherein the petrolatum-based composition further comprises at least one additional anti-fungal agent selected from the group consisting of terbinafine HCl, ciclopirox, ciclopirox olamine, fluconazole, itraconazole, ketoconazole, amorolfine, efinaconazole, clotrimazole, miconazole (miconazole nitrate) and any combination thereof.

Statement 124: A method according to Statement 123, wherein the one or more cationic biocides and the at least one additional anti-fungal agent are dissolved in a polar solvent to form a cationic biocide solution, the cationic biocide solution dispersed in the petrolatum to form a stable suspension.

Statement 125: A method according to claim any one of the preceding Statements 120-124, wherein the polar solvent is selected from the group consisting of water, ethanol, and any combination thereof.

Statement 126: A method according to any one of the preceding Statements 91-125, wherein the petrolatum-based composition further comprises from about 0.01% to about 5%, or from about 0.001% to about 5%, or from about 0.05% to about 5% by weight terbinafine HCl.

Statement 127: A method according to any one of the preceding Statements 91-125, wherein the petrolatum-based composition further comprises from about 0.01% to about 5%, or from about 0.001% to about 5%, or from about 0.05% to about 5% by weight ciclopirox.

Statement 128: A method according to any one of the preceding Statements 91-125, wherein the petrolatum-based composition further comprises from about 0.01% to about 5%, or from about 0.001% to about 5%, or from about 0.05% to about 5% by weight ciclopirox olamine.

Statement 129: A method according to any one of the preceding Statements 91-125, wherein the petrolatum-based composition further comprises from about 0.01% to about 5%, or from about 0.001% to about 5%, or from about 0.05% to about 5% by weight fluconazole.

Statement 130: A method according to any one of the preceding Statements 91-125, wherein the petrolatum-based composition further comprises from about 0.01% to about 5%, or from about 0.001% to about 5%, or from about 0.05% to about 5% by weight itraconazole.

Statement 131: A method according to any one of the preceding Statements 91-125, wherein the petrolatum-based composition further comprises from about 0.01% to about 5%, or from about 0.001% to about 5%, or from about 0.05% to about 5% by weight ketoconazole.

Statement 132: A method according to any one of the preceding Statements 91-125, wherein the petrolatum-based composition further comprises from about 0.01% to about 5%, or from about 0.001% to about 5%, or from about 0.05% to about 5% by weight amorolfine.

Statement 133: A method according to any one of the preceding Statements 91-125, wherein the petrolatum-based composition further comprises from about 0.01% to about 5%, or from about 0.001% to about 5%, or from about 0.05% to about 5% by weight efinaconazole.

What is claimed is:

1. A method of treating onychomycosis in a subject, the method comprising applying a petrolatum-based polyhexamethylene biguanide (PHMB) composition to the nail of a subject in need of treatment, wherein the petrolatum-based PHMB composition comprises greater than about 85% petrolatum and from about 0.05% to about 2.5% by weight PHMB.

2. The method according to claim 1, wherein the onychomycosis is caused by *Trichophyton rubrum* (*T. rubrum*).

3. The method according to claim 1, wherein the onychomycosis is caused by *Candida*.

4. The method according to claim 3, wherein the Candidal onychomycosis is caused by *Candida auris* (*C. auris*).

5. The method according to claim 4, wherein the *C. auris* is multi-drug resistant *C. auris*.

6. The method according to claim 1, wherein the petrolatum-based PHMB composition comprises from about 0.1% to about 1% by weight PHMB.

7. The method according to claim 6, wherein the petrolatum-based PHMB composition comprises greater than about 90% by weight petrolatum.

8. The method according to claim 7, wherein the petrolatum-based PHMB composition excludes an added emulsifier.

9. The method according to claim 7, wherein the petrolatum-based PHMB composition further includes one or more cationic biocides selected from the group consisting of polyaminopropyl biguanide (PAPB), benzalkonium chloride, cetrimide, chlorhexidine, and any combination thereof.

10. The method according to claim 9, wherein the total amount of the one or more cationic biocides is less than 1% by weight of the petrolatum-based PHMB composition.

11. The method according to claim 7, wherein the petrolatum-based PHMB composition is prepared by a process comprising:

a) dissolving the PHMB in a polar solvent to give a PHMB solution;
b) heating the petrolatum to a temperature sufficient to cause the petrolatum to melt to give a melted petrolatum and heating the PHMB solution to a temperature higher than the temperature of the melted petrolatum to give a heated PHMB solution;
c) mixing the melted petrolatum and the heated PHMB solution to give a melted mixture; and
d) cooling the melted mixture to give the petrolatum-based PHMB composition.

12. The method according to claim 11, wherein the heated PHMB solution has a temperature that is about 1° C. to about 5° C. higher than the temperature of the melted petrolatum.

13. The method according to claim 12, wherein the PHMB is dissolved in a polar solvent to form a PHMB solution, the PHMB solution dispersed in the petrolatum to form a stable suspension.

14. The method according to claim 7, wherein the petrolatum-based PHMB composition further comprises at least one additional anti-fungal agent selected from the group consisting of terbinafine HCl, ciclopirox, ciclopirox olamine, fluconazole, itraconazole, ketoconazole, amorolfine, efinaconazole, clotrimazole, miconazole (miconazole nitrate) and any combination thereof.

15. The method according to claim 14, wherein the petrolatum-based PHMB composition comprises from about 0.5% to about 1.5% by weight of the at least one additional anti-fungal agent.

16. The method according to claim 11, wherein the polar solvent is selected from the group consisting of water, ethanol, and any combination thereof.

17. The method according to claim 7, wherein the petrolatum-based PHMB composition further comprises from about 0.5% to about 1.5% by weight terbinafine HCl.

18. The composition according to claim 7, wherein the petrolatum-based PHMB composition further comprises from about by 0.5% to about 1.5% by weight ciclopirox.

19. The composition according to claim 7, wherein the petrolatum-based PHMB composition further comprises from about 0.5% to about 1.5% by weight ciclopirox olamine.

20. A method of treating a fungal infection of the nail, the method comprising applying a petrolatum-based composition comprising a petrolatum-based polyhexamethylene biguanide (PHMB) composition to the nail of a subject in need of treatment, wherein the petrolatum-based PHMB composition comprises from about 0.05% to about 2.5% by weight PHMB and greater than about 85% by weight petrolatum; and wherein the petrolatum-based PHMB composition is prepared by a process comprising:

a) dissolving the PHMB in a polar solvent to give a PHMB solution;
b) heating the petrolatum to a temperature sufficient to cause the petrolatum to melt to give a melted petrolatum and heating the PHMB solution to a temperature higher than the temperature of the melted petrolatum to give a heated PHMB solution;
c) mixing the melted petrolatum and the heated PHMB solution to give a melted mixture; and
d) cooling the melted mixture to give the petrolatum-based PHMB composition.

* * * * *